(12) United States Patent
Bivin et al.

(10) Patent No.: US 8,114,052 B2
(45) Date of Patent: Feb. 14, 2012

(54) FLUID DELIVERY DEVICE WITH VARIABLE FORCE SPRING

(76) Inventors: Donald B. Bivin, Oakland, CA (US);
Marshall S. Kriesel, St. Paul, MN (US);
Joshua W. Kriesel, San Francisco, CA (US); Alan D. Langerud, Plymouth, MN (US)

(*) Notice: Subject to any disclaimer, the term of this patent is extended or adjusted under 35 U.S.C. 154(b) by 0 days.

(21) Appl. No.: 12/802,054

(22) Filed: May 28, 2010

(65) Prior Publication Data
US 2010/0241074 A1 Sep. 23, 2010

Related U.S. Application Data

(63) Continuation-in-part of application No. 11/982,644, filed on Oct. 31, 2007, now Pat. No. 7,828,770.

(51) Int. Cl.
*A61M 37/00* (2006.01)
(52) U.S. Cl. ........................................ 604/132
(58) Field of Classification Search ............... 604/132
See application file for complete search history.

(56) References Cited

U.S. PATENT DOCUMENTS
6,056,716 A * 5/2000 D'Antonio et al. ............ 604/68
2005/0277882 A1* 12/2005 Kriesel ......................... 604/131

FOREIGN PATENT DOCUMENTS
WO WO 2009010591 A2 * 1/2009
* cited by examiner

*Primary Examiner* — Nicholas Lucchesi
*Assistant Examiner* — Jason Flick
(74) *Attorney, Agent, or Firm* — James E. Brunton

(57) ABSTRACT

A compact fluid dispenser for use in controllably dispensing fluid medicaments, such as antibiotics, blood clotting agents, analgesics, and like medicinal agents from collapsible containers at a uniform rate. The dispenser includes a novel stored energy source that is provided in the form of a compressible-expandable member that functions to continuously and uniformly expel fluid from the apparatus reservoir. The apparatus further includes a novel fluid flow control assembly that precisely controls the flow of the medicament solutions from the apparatus reservoir to the patient.

20 Claims, 31 Drawing Sheets

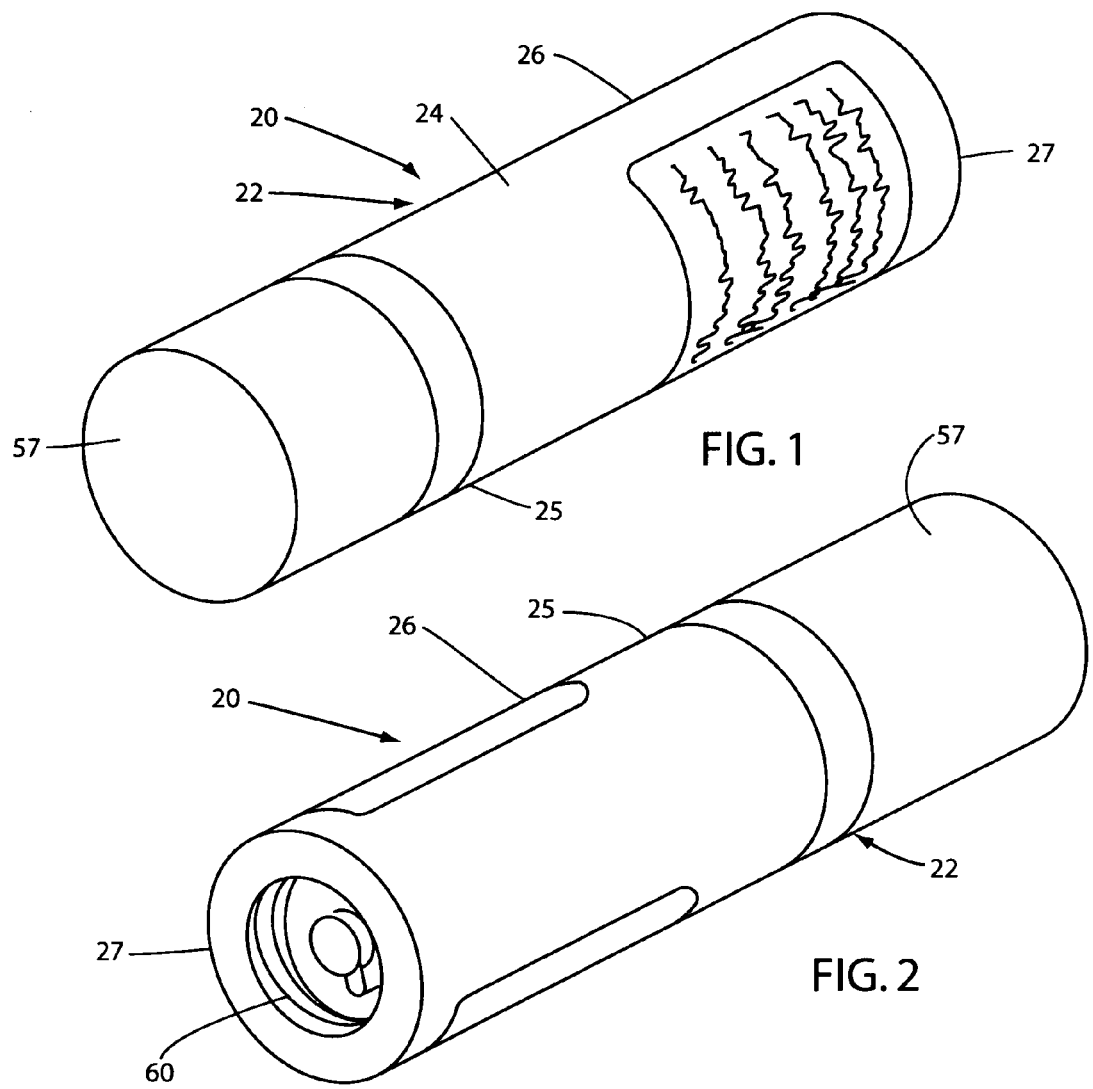

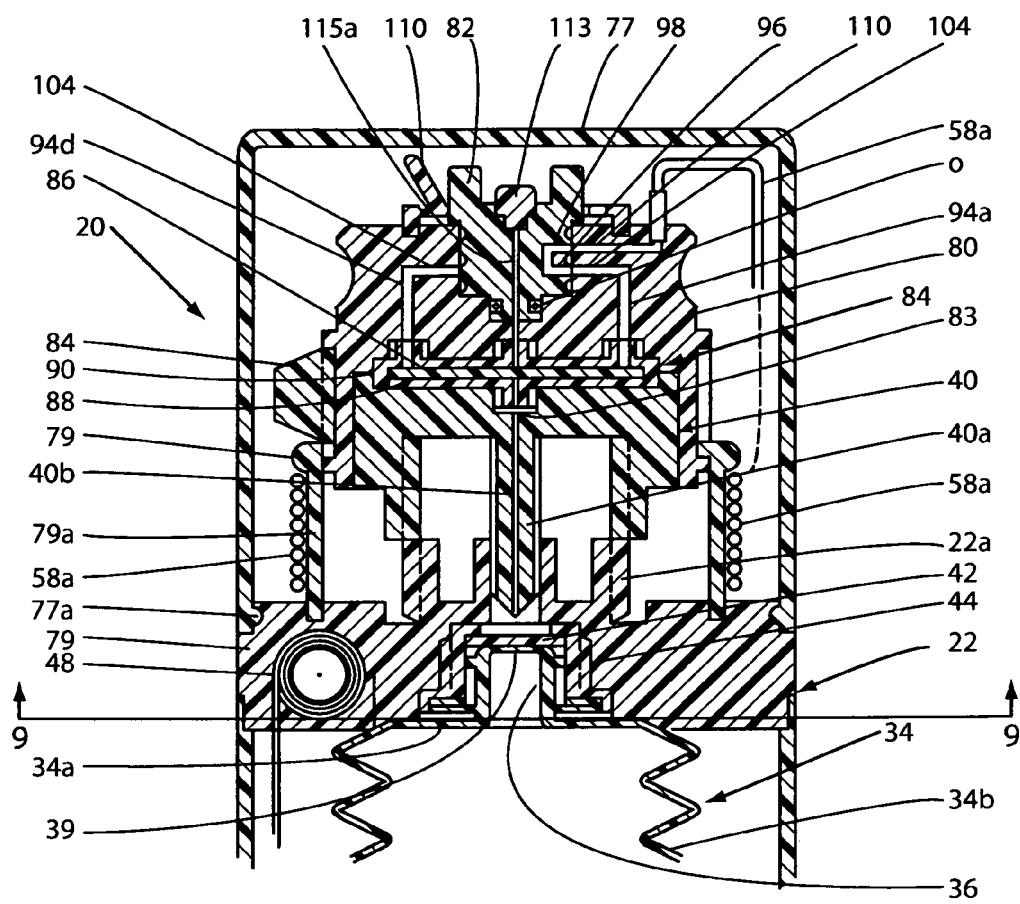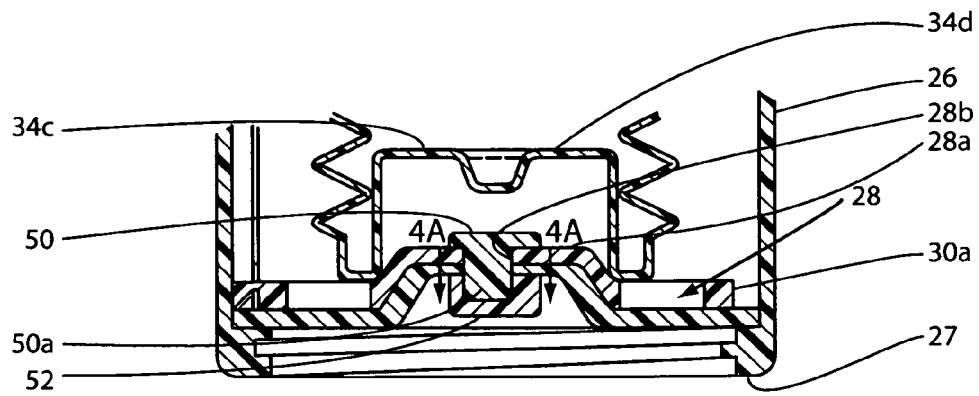
FIG. 4

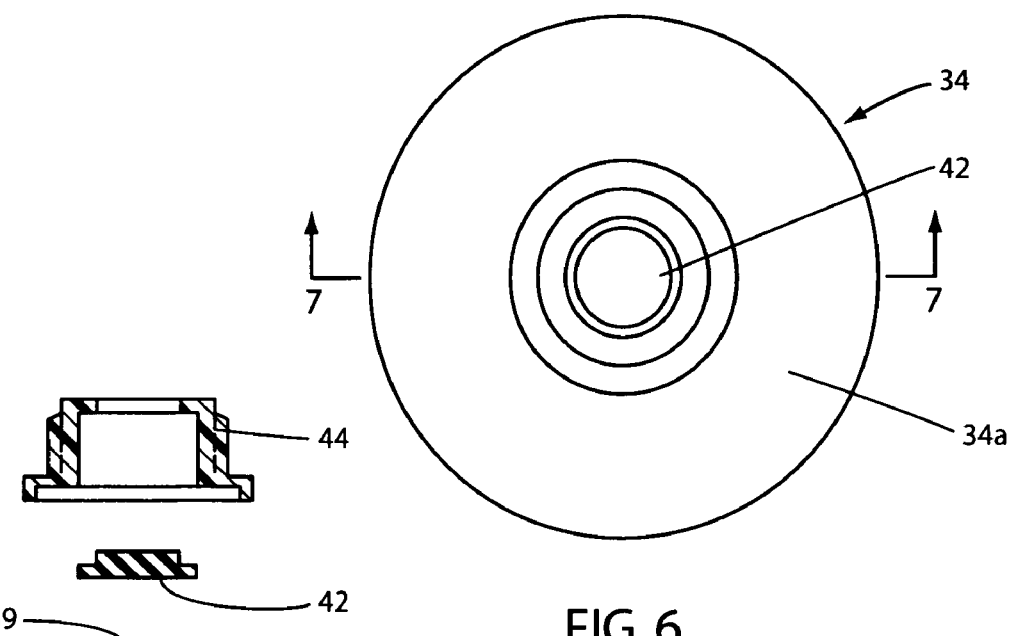
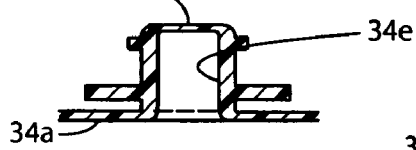
FIG. 6
FIG. 8
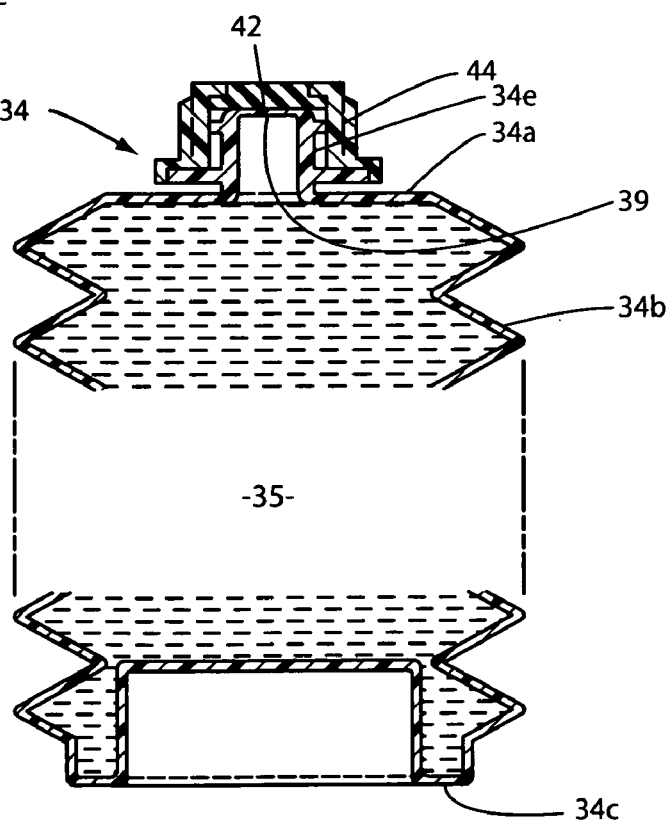
FIG. 7

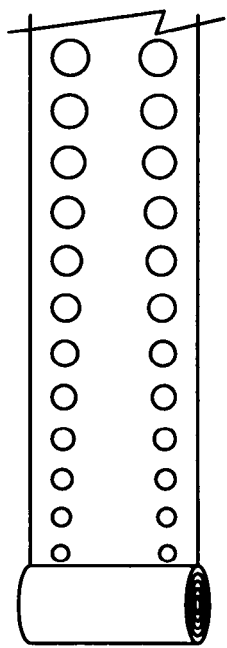
FIG. 31
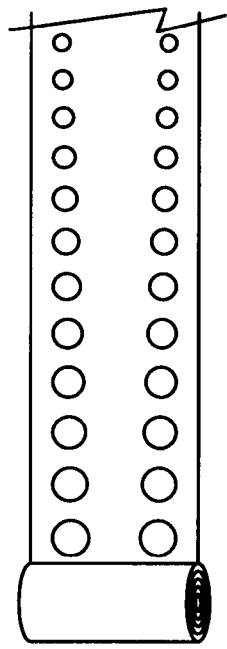
FIG. 32
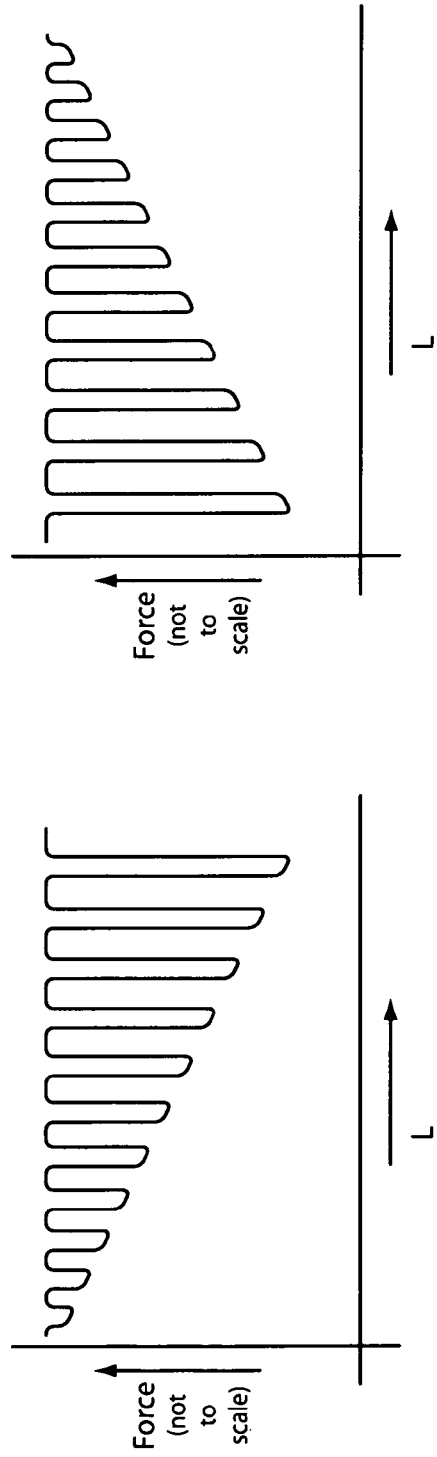
FIG. 31A
FIG. 32A

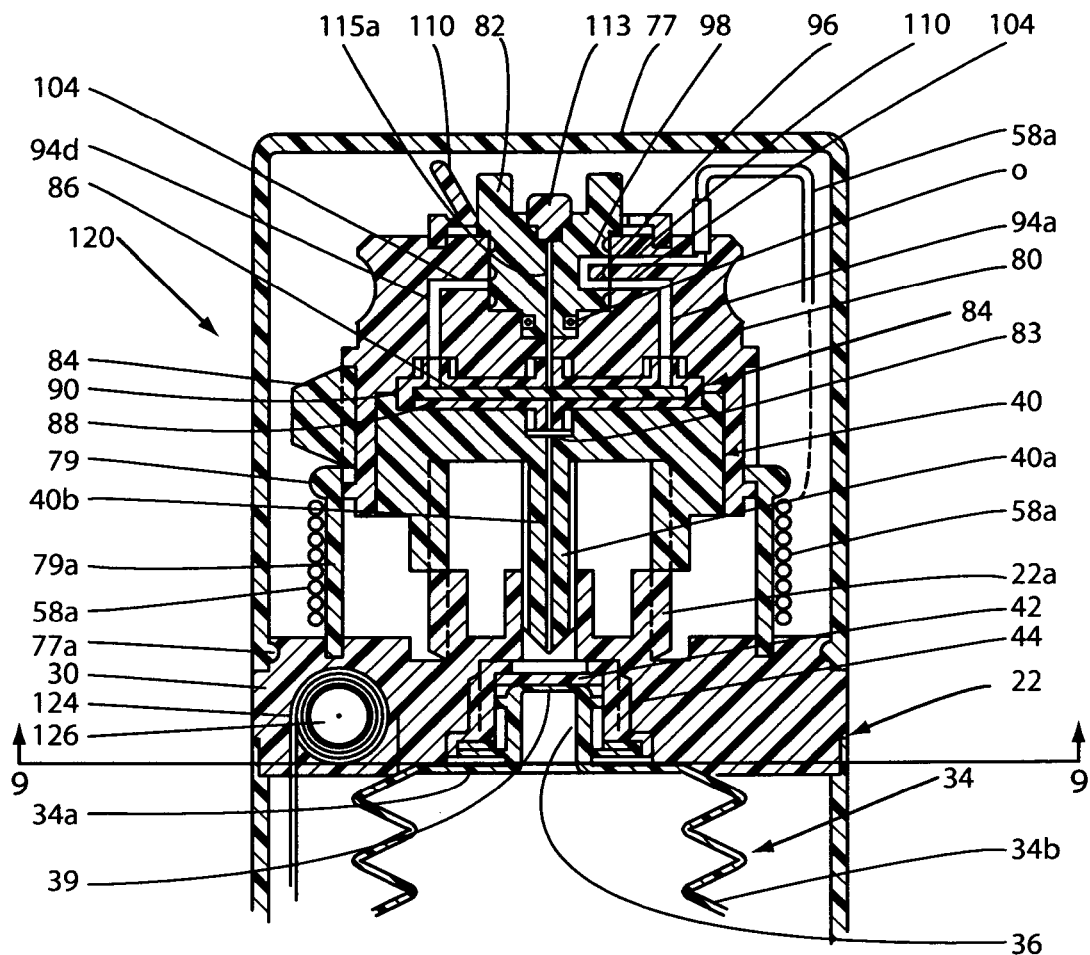
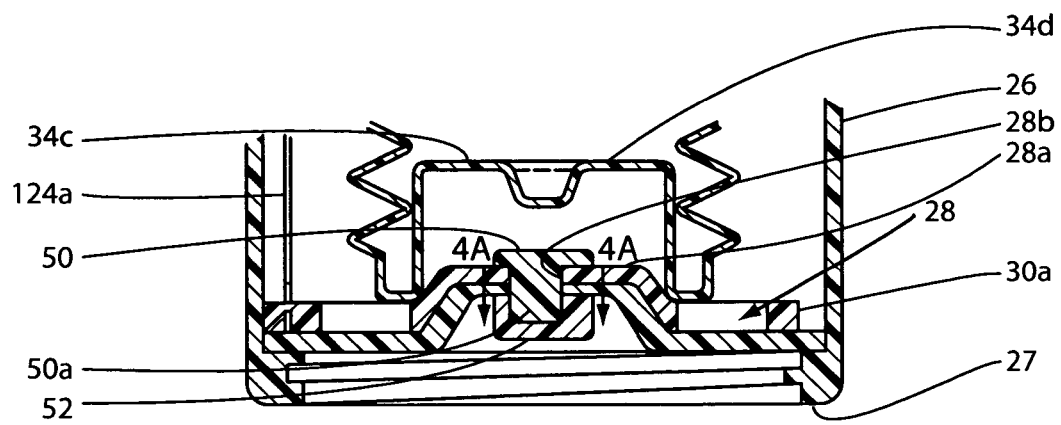
FIG. 34

FLUID DELIVERY DEVICE WITH VARIABLE FORCE SPRING

CROSS-REFERENCE TO RELATED APPLICATIONS

This application is a Continuation-In-Part of co-pending U.S. Ser. No. 11/982,644 filed on Oct. 31, 2007 now U.S. Pat. No. 7,828,770.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates generally to fluid dispensing apparatus. More particularly, the invention concerns a medicament delivery device for dispensing medicinal fluids to ambulatory patients that includes a novel stored energy source in the form of a variable force spring. The variable force spring is cooperatively associated with the collapsible reservoir of the device and functions to deliver a variable force to the reservoir that tends to urge fluid flow therefrom at a substantially constant rate. In one form of the invention the stored energy source uniquely comprises an elongated, pre-stressed strip of spring material that is formed into coils and exhibits a cross-sectional mass that varies along its length. In another form of the invention, the band portion of the spring is coiled about its spring drum in predetermined varying degrees of tightness to achieve highly specific and desirable linear and non-linear force-distention curves to meet the fluid delivery requirements of the invention.

2. Description of Related Art Including Information Disclosed Under 37 CFR 1.97 and 1.98

A number of different types of medicament dispensers for dispensing medicaments to ambulatory patients have been suggested in the past. Many of the devices or apparatus seek either to improve or to replace the traditional gravity flow and hypodermic syringe methods which have been the standard for delivery of liquid medicaments for many years.

The prior art gravity flow methods typically involve the use of intravenous administration sets and the familiar flexible solution bag suspended above the patient. Such gravimetric methods are cumbersome, imprecise and require bed confinement of the patient. Periodic monitoring of the apparatus by the nurse or doctor is required to detect malfunctions of the infusion apparatus. Accordingly, the prior art devices or apparatus are not well suited for use in those instances where the patient must be transported to a remote facility for treatment.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to one of the present applicants, namely U.S. Pat. No. 5,743,879, discloses an injectable medicament dispenser for use in controllably dispensing fluid medicaments such as insulin, anti-infectives, analgesics, oncolylotics, cardiac drugs, bio-pharmaceuticals, and the like from a pre-filled container at a uniform rate. The dispenser, which is quite dissimilar in construction and operation from that of the present invention, includes a stored energy source in the form of a compressively deformable, polymeric, elastomeric member that provides the force necessary to controllably discharge the medicament from a pre-filled container, which is housed within the body of the apparatus. After having been deformed, the polymeric, elastomeric member will return to its starting configuration in a highly predictable manner.

BRIEF SUMMARY OF THE INVENTION

By way of brief summary, one form of the fluid delivery device of the present invention for dispensing medicaments to a patient comprises a supporting structure; a carriage assembly interconnected with the supporting structure for movement between a first position and a second position; a pre-filled collapsible container carried by the carriage assembly, the collapsible container having accessing means for accessing the reservoir comprising a frangible member in the form of a pierceable member or shearable member. The apparatus also includes guide means connected to the supporting structure for guiding travel of the carriage assembly between the first position and said second positions; a stored energy source operably associated with the carriage assembly for moving the carriage assembly between the first and second positions; and an administration set, including an administration line interconnected with the outlet port of the collapsible reservoir. The stored energy source is cooperatively associated with the collapsible container of the device and functions to deliver a variable force to the container that tends to urge fluid flow therefrom at a substantially constant rate. In one form of the invention the stored energy source uniquely comprises an elongated, pre-stressed strip of spring material that is formed into coils and exhibits a cross-sectional mass that varies along its length. In another form of the invention, the band portion of the spring is coiled about its spring drum in predetermined varying degrees of tightness to achieve highly specific and desirable linear and non-linear force-distention curves to meet the fluid delivery requirements of the invention.

Another object of the invention is to provide a compact fluid delivery device of the character described in the preceding paragraph in which variation in cross-sectional mass along the length of the retractable spring can be achieved by varying the width of the pre-stressed spring along its length.

Another object of the invention is to provide a compact fluid delivery device of the character described in which variation in cross-sectional mass along the length of the retractable spring can be achieved by providing spaced-apart apertures in the pre-stressed spring along its length.

Another object of the invention is to provide a compact fluid delivery device of the character described in which the band portion of the spring is coiled about its spring drum in predetermined varying degrees of tightness to achieve highly specific and desirable linear and non-linear force-distention curves to meet the fluid delivery requirements of the invention.

With the forgoing in mind, it is still another object of the present invention to provide a compact fluid delivery device for use in controllably dispensing fluid medicaments to ambulatory patients, such as, antibiotics, blood clotting agents, analgesics, KVO, artificial blood substitutes, resuscitation fluids, internal nutritional solutions, biologics, and like beneficial agents from pre-filled or field-filled containers at a uniform rate.

Another object of the invention is to provide a small, compact pre-filled fluid dispenser that is aseptically filled and sealed at the time of manufacture.

Another object of the invention is to provide an apparatus that is of simple construction that can be used in the field with a minimum amount of training.

Another object of the invention is to provide a dispenser in which a stored energy source is provided in the form of a highly novel variable force retractable member of a unique construction that provides the force necessary to continuously and uniformly expel fluid from the apparatus reservoir.

Another object of the invention is to provide a dispenser of the class described which includes a fluid flow control assembly that precisely controls the flow of the medicament solution to the patient. Uniquely, the container is formed as a unitary structure that includes a collapsible side wall and a pierceable closure wall that isolates the beneficial agents contained within the container reservoir from external contaminants.

Another object of the invention is to provide a dispenser that includes precise variable flow rate selection.

Another object of the invention is to provide a fluid dispenser of the class described which is compact, lightweight, is easy for ambulatory patients to use, is fully disposable, transportable and is extremely reliable in operation.

Another object of the invention is to provide a fluid dispenser as described in the preceding paragraphs that is easy and inexpensive to manufacture in large quantities.

BRIEF DESCRIPTION OF SEVERAL VIEWS OF THE DRAWINGS

FIG. 1 is a generally perspective, top view of one form of the fluid delivery device of the present invention for dispensing medicaments to a patient.

FIG. 2 is a generally perspective, bottom view of the fluid delivery device shown in FIG. 1.

FIG. 4 is a foreshortened, longitudinal, cross-sectional view of the device showing the reservoir in a pre-filled condition.

FIG. 4A is a cross-sectional view taken along lines 4A-4A of FIG. 4.

FIG. 6 is a top plan view of the collapsible container of this embodiment of the invention.

FIG. 7 is a cross-sectional view taken along lines 7-7 of FIG. 6.

FIG. 8 is an exploded, cross-sectional view of the reservoir access assembly of this form of the invention.

FIG. 31 is a generally illustrative view of the retractable spring of a seventeenth modified configuration.

FIG. 31A is a generally graphical representation plotting force exerted by the spring shown in FIG. 31 versus position along the length of the spring.

FIG. 32 is a generally illustrative view of the retractable spring of a eighteenth modified configuration.

FIG. 32A is a generally graphical representation plotting force exerted by the spring shown in FIG. 32 versus position along the length of the spring.

FIG. 34 is a foreshortened, longitudinal, cross-sectional view of an alternate form of the device of the invention showing the reservoir in a pre-filled condition.

FIG. 36A is a view taken along lines 36A-36A of FIG. 36.

DETAILED DESCRIPTION OF THE INVENTION

Figure 3:
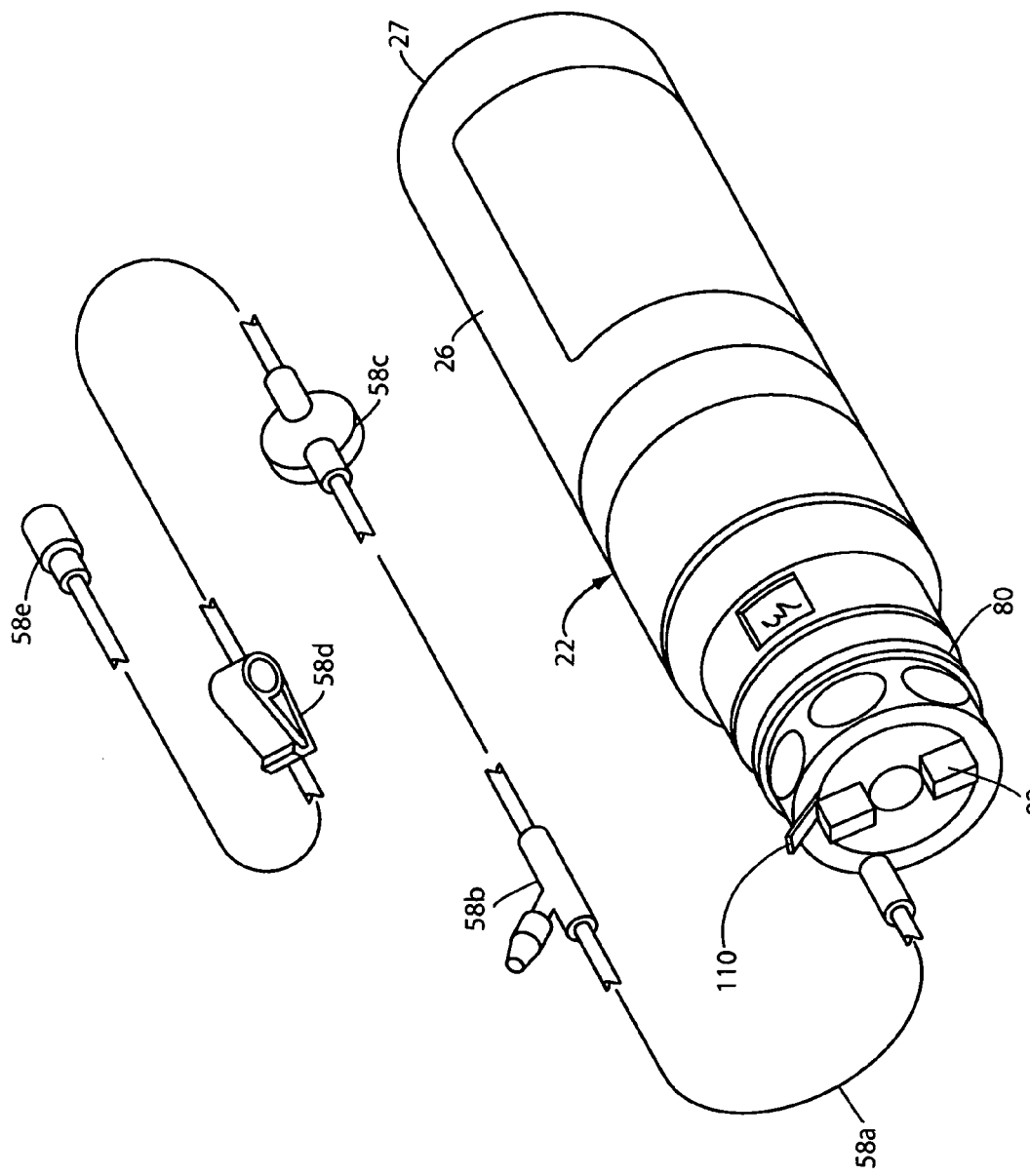
FIG. 3 is a generally perspective, exploded view of the fluid delivery device of the invention showing the top cover removed and the administration set unfurled.

Definitions: As used herein, the following terms have the following meanings:

Constant Force Spring

Constant force springs are a special variety of extension spring. They are tightly coiled wound bands of pre-hardened spring steel or stainless steel strip with built-in curvature so that each turn of the strip wraps tightly on its inner neighbor. When the strip is extended (deflected) the inherent stress resists the loading force; the same as a common extension spring, but at a nearly constant (zero) rate. The constant-force spring is well suited to long extensions with no load build-up. In use, the spring is usually mounted with the internal diameter (ID) tightly wrapped on a drum and the free end attached to the loading force. Considerable flexibility is possible with constant-force springs because the load capacity can be multiplied by using two or more strips in tandem, or back-to-back. Constant force springs are available in a wide variety of sizes.

Force Generating Region

The force generating region of the prior art constant force spring means the region of the spring in which the force is generated. More particularly, it should be understood that it is the change in radius of curvature of the prior art constant force spring that is responsible for the generation of the force produced by the spring. In fact, the radius of curvature of the prior art constant for spring changes from essentially infinity to a value equal to the radius of the spool on which the spring is wound.

Note that because the force generating region takes up some portion of the length of the spring it will tend to average any point-by-point changes in physical or structural properties of the spring.

It should also be kept in mind that this force generating region takes up some part of the total length of the spring, and that this force generating region moves as the degree of extension of the spring changes.

Modified Constant Force Spring (Variable Force Spring)

The modified constant force spring or variable force spring of the present invention comprises a spring of highly novel configuration that includes an elongated, pre-stressed strip of spring material that may be metal, a polymer, a plastic, or a composite material with built-in curvature so that, like the conventional constant force spring, each turn of the strip wraps tightly on its inner neighbor. Uniquely, the elongated pre-stressed strip of spring material exhibits a cross-sectional mass that varies along said length. This variation in cross-sectional mass along the length of the spring can be achieved in various ways, as for example, by varying the width of the pre-stressed strip along its length and by providing spaced-apart apertures in the pre-stressed strip along its length.

Mass of Material

The term "mass of material" when used herein in connection with the modified constant force spring of the invention means the mass of material in the "force generating region" as previously defined herein. More particularly, increasing the mass of material in the "force generating region" will increase the force provided by the spring. Conversely, decreasing the mass of material in the "force generating region" will result in a reduction of the force generated by the spring. The mass in the active region can be changed by changing the thickness of the spring, the width of the spring, the density of material of the spring, or any combination of these.

Unitary Container

A closed container formed from a single component.

Continuous/Uninterrupted Wall.

A wall having no break in uniformity or continuity.

Hermetically Sealed Container

A container designed and intended to be secure against the entry of microorganisms and to maintain the safety and quality of its contents after pressurizing.

Biologic

A virus, therapeutic serum, toxin, antitoxin, vaccine, blood, blood component or derivative, allergenic product, or analogous product applicable to the prevention, treatment or cure of diseases or injuries of man.

Drug

As defined by the Food, Drug and Cosmetic Act, drugs are "articles (other than food) intended for the use in the diagnosis, cure, mitigation, treatment, or prevention of disease in man or other animals, or to affect the structure or any function."

Drug Product

A finished dosage form (e.g. tablet, capsule, or solution) that contains the active drug ingredient usually combined with inactive ingredients.

Artificial Blood Substitutes

Blood Substitutes are used to fill fluid volume and/or carry oxygen and other gases in the cardiovascular system. These include volume expanders for inert products, and oxygen therapeutics for oxygen-carrying products.

Resuscitation Fluids

Infusion of hyperosmotic-hyperoncotic solutions such as hypertonic saline dextran (HSD) as used for resuscitation of traumatic shock and perioperative volume support or as an adjunct to other conventional isotonic crystalloid solutions. Where hypotension is caused by myocardial depression, pathological vasodilatation and extravascation of circulating volume due to widespread capillary leak, a resuscitative effort is attempted to correct the absolute and relative hypovolemia by refilling the vascular tree. Here resuscitation with a small volume of hypertonic-hyperoncotic solution allows systemic and splancnic hemodynamic and oxygen transport recovery, without an increase in pulmonary artery pressure. Alternate types of normotonic, hyperoncotic, hypertonic, and hypertonic-hyperoncotic solutions can be used for systemic hemodynamic recovery.

KVO

KVO—keeping-the-vein-open in an IV set up, a phrase that refers to the flow rate of a maintenance IV line established as a prophylactic access.

Nutritionals

Dietary supplemental enteral nutrition support feeding solutions used for nasoenteric application typically used in nasogastric, nasoduodenal and nasojejunal or intravenous routes of administration.

Beneficial Agent

The term beneficial agent can include any substance or compound that is biologically active and includes any physiologically or pharmacologically active substance that produces a localized or systemic effect in humans or animals and that can be delivered by the present invention to produce a beneficial and useful result.

Diluent

A liquid that dilutes, as in an inert solution used to dilute a medicament. An inert liquid carrier of a beneficial agent.

Device

An instrument, apparatus, implement, machine, contrivance, implant, in vitro reagent, or other similar or related article, including any component, part or accessory, which is intended for use in the diagnosis, cure, treatment or prevention of disease. A device does not achieve its intended purpose through chemical action in the body and is not dependent upon being metabolized to achieve its purpose.

Reservoir

A receptacle or chamber for storing a fluid. A part of a machine, apparatus, where liquid is stored.

Liquid Container

A receptacle for holding a liquid. A fluid dispenser that is carried or transported.

Collapsible

To cause to fold, break down, or fall down or inward or as in bent-over or doubled-up so that one part lies on another.

Collapsible Container

A dispensing apparatus in which one or more walls of the container are made of a material which will deform (collapse) when pressure is applied thereto; or a dispensing apparatus having a collapsible or telescoping wall structure.

Aseptic Processing

The term 'aseptic processing' as it is applied in the pharmaceutical industry refers to the assembly of sterilized components and product in a specialized clean environment.

Sterile Product

A sterile product is one that is free from all living organisms, whether in a vegetative or spore state.

Blow-Fill-Seal Process

The concept of aseptic blow-fill-seal (BFS) is that a container is formed, filled, and sealed as a unitary container in a continuous manner without human intervention in a sterile enclosed area inside a machine. The process is multi-stepped, pharmaceutical grade resin is extruded into a tube, which is then formed into a container. A mandrel is inserted into the newly formed container and filled. The container is then sealed, all inside a sterile shrouded chamber. The product is then discharged to a non-sterile area for packaging and distribution.

Integrally Formed

An article of one-piece construction, or several parts that are rigidly secured together and is smoothly continuous in form and that any such components making up the part have been then rendered inseparable.

Frangible

An article, item or object that is capable of being ruptured or broken, but does not necessarily imply any inherent materials weakness. A material object, under load that demonstrates a mechanical strain rate deformation behavior, leading to disintegration.

Luer Lock Connector

A connector used to connect medical apparatus. Classically, the Luer consists of a tapered barrel and a conical male part that fits into it with or without a seal.

Referring to the drawings and particularly to FIGS. 1 through 3, one form of the fluid dispensing apparatus of the present invention for dispensing medicaments to a patient is there shown and generally designated by the numeral 20. The dispensing apparatus here comprises a supporting structure 22, which includes a housing 24 having an upper portion 25 and a generally cylindrically shaped skirt portion 26. Supporting structure 22 can be constructed from metal, plastic or any suitable material. Connected to portion 26 is a base segment 27, the details of construction of which will presently be described.

Figure 5:
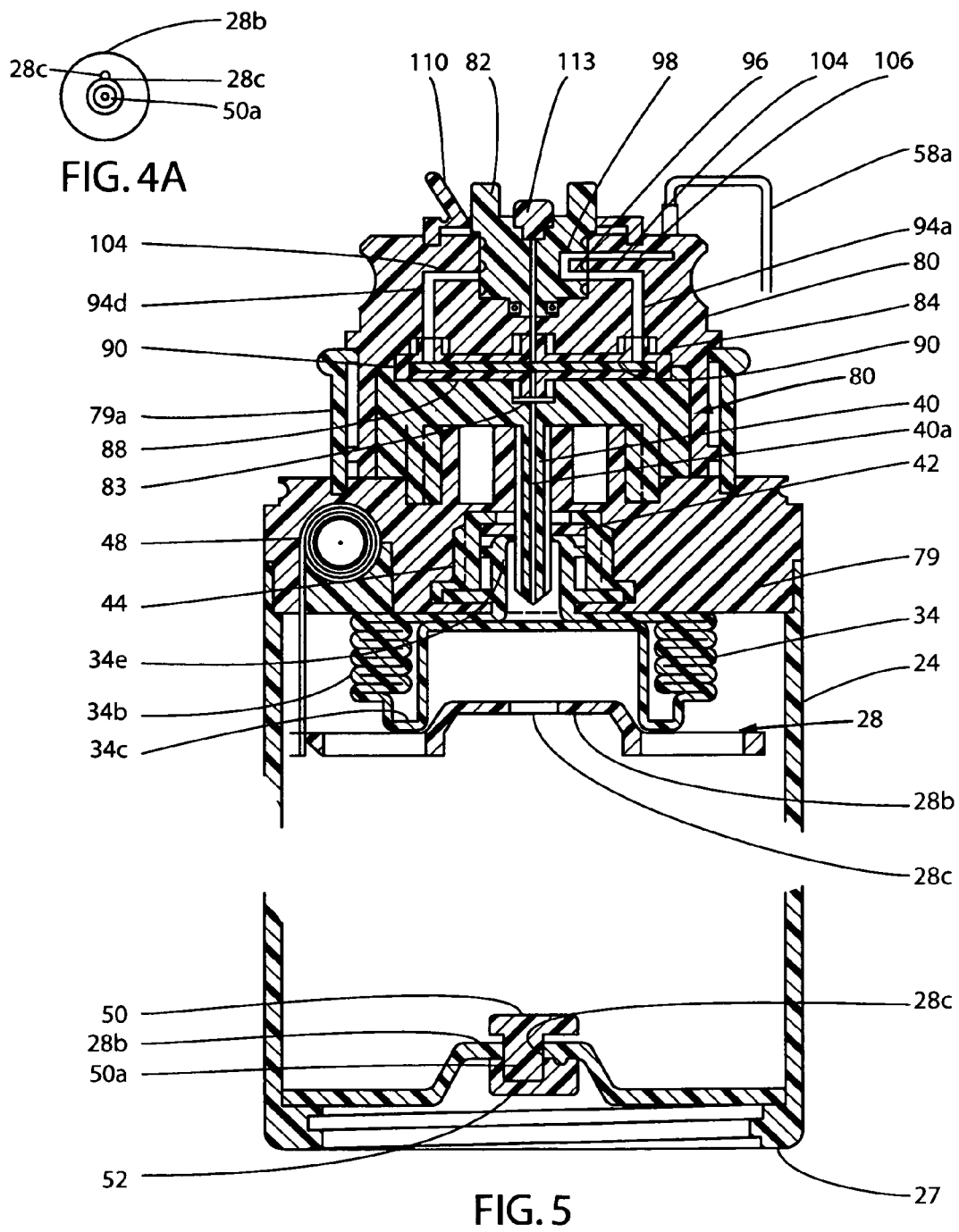
FIG. 5 is a foreshortened, longitudinal, cross-sectional view, similar to FIG. 4, but showing the various components of the apparatus as they appear following delivery to the patient of the fluid contained within the device reservoir with the reservoir substantially empty.

Disposed within skirt portion 26 is a carriage assembly 28 which is movable between a first position shown in FIG. 4 and a second position shown in FIG. 5. Carriage assembly 28 here comprises a carriage 30 having a carriage flange 30a to which the novel stored energy means of the present invention is operably interconnected. Carriage assembly 28 is releasably locked in its first position by a novel locking means the character of which will be described in the paragraphs which follow.

Carried by carriage assembly 28 is a reservoir defining assembly 34 that defines a fluid reservoir 35. As illustrated in FIGS. 4, 5, 6 and 7, reservoir defining assembly 34 includes a top wall 34a, a continuous bellows-like sidewall 34b that is connected to top wall 34a and a bottom wall 34c that is connected to side wall 34b. Bellows-like sidewall 34b is movable from the expanded, starting configuration shown in FIG. 4 to the collapsed configuration shown in FIG. 5. As illustrated in FIGS. 4 and 7, bottom wall 34c includes a cup-shaped portion 34d.

This important reservoir defining container also includes a neck portion 34e which is sealed at the time of manufacture by a thin closure wall 39. Neck portion 34e forms a part of the novel reservoir access means of the invention the purpose of which will presently be described. As shown in FIG. 5, when the bellows-like side wall 34b is collapsed, the cup-shaped portion 34d is disposed in close proximity to the neck portion 34e and substantially fills the upper portion of the collapsible container. In this embodiment of the invention fluid reservoir 35 is accessible via a penetrating member 40a that is carried by the septum-penetrating assembly generally designated in FIG. 4 by the numeral 40. Penetrating member 40a is adapted to pierce closure wall 39 as well as a pierceable membrane 42 which is positioned over closure wall 39 by means of a closure cap 44 which is affixed to the neck portion 34c of the container assembly (see also FIGS. 7 and 8).

Closure wall 39 is integrally formed with neck portion 34e by means of a novel aseptic blow-fill-seal technique that is also used to form reservoir defining assembly 34. This aseptic blow-fill-seal technique comprises the continuous extrusion through an extruder head of a length of a parison in the form of a hollow tube between and through two co-acting first or main mold halves. The method includes the step of cutting off the parison below the extruder head and above the main mold halves to create an opening which allows a blowing and filling nozzle assembly to be moved downwardly into the opening in the parison for molding and thereafter filling a molded container.

When the container portion of the container assembly is filled with the desired amount of liquid, the blowing and filling nozzle assembly is retracted from the opening in the parison. A separate pair of co-acting second or upper sealing mold halves are then moved together around the exposed length of parison to form and seal the container upper portion. The finished container assembly, completely formed, filled, and sealed as a unitary structure is then conveyed out of the molding apparatus. Further information concerning aseptic blow-fill and blow-fill-seal techniques is available from Rommelag of Waiblingen, Germany and is discussed in U.S. Letters Pat. No. RE 27,155 issued to Hansen. Because of the pertinence of this latter patent, U.S. Pat. No. RE 27,155 is hereby incorporated by reference as though fully set forth herein.

The basic unitary container and the hermetically sealed reservoir portion of the container are closed by the thin closure wall 39. Following closure of the container by the thin closure wall 39, the piercable septum membrane 42 is then positioned over the closure wall and the cap 44 is positioned over the piercable septum and secured to neck portion 34e by any suitable means such as adhesive bonding or sonic welding. It is to be understood that septum 42 can also be constructed as a slit or partially slit member. It is important to note that closure wall 39 effectively prevents the medicament contained within the fluid reservoir from coming in contact with external contaminants.

To controllably move the carriage assembly 28 from its first position to its second position, novel stored energy means are provided. This novel stored energy means, which is operably associated with carriage assembly, is here provided in the form of three uniquely formed variable force springs 48 (FIG. 9), the character of which will presently be described.

As illustrated in FIGS. 4, 4A and 5 the carriage locking means includes a locking member 50 having a shank portion 50a which extends through a keyhole-shaped opening 28c provided in the carriage base 28b (see FIG. 4A). The carriage locking means also includes a finger-engaging, operating member 52 that is connected to shank portion 50a. Operating member 52 functions to rotate locking member 50 from a transverse locking position to a release position in alignment with keyhole opening 28c formed in carriage base 28b. As the operating member is rotated from a locked position to a release position, the stored energy means, or springs 48 (FIGS. 4 and 9) will move the carriage from a position shown in FIG. 4 into the position shown in FIG. 5 and in so doing will urge the fluid contained within reservoir 35 to flow toward penetrating member 40, into passageway 40b formed in the penetrating member and toward the rate control means of the invention, the construction and operation of which will presently be described.

Figure 10:
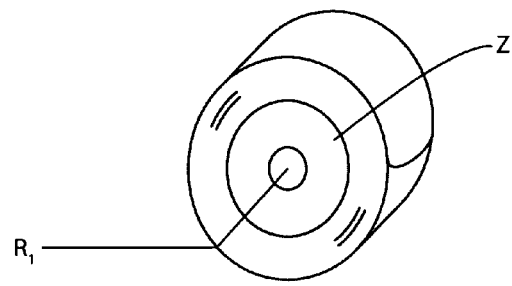
FIG. 10 is a generally perspective view of a prior art retractable spring.

Turning now to a consideration of the stored energy sources, or variable force springs 48, which form an extremely important feature of the present invention, it is to be understood that the objective of many prior art fluid and drug delivery systems is to deliver fluid at a constant flow rate. One method for achieving a constant flow rate over time involves ensuring that the pressure driving the fluid through the device is constant, i.e., the pressure inside the fluid reservoir of the device is constant. In the present invention achieving constant pressure in the bellows-like fluid reservoir 35 of the device is an accomplished in a unique manner by modifying a typical constant force spring, such as a Negator spring "NS". Negator springs, which are of the general character illustrated in FIGS. 10 and 11 of the drawings, are readily commercially available from a number of sources including Stock Drive Products/Sterling Instruments of New Hyde Park, N.Y.

Figure 11:
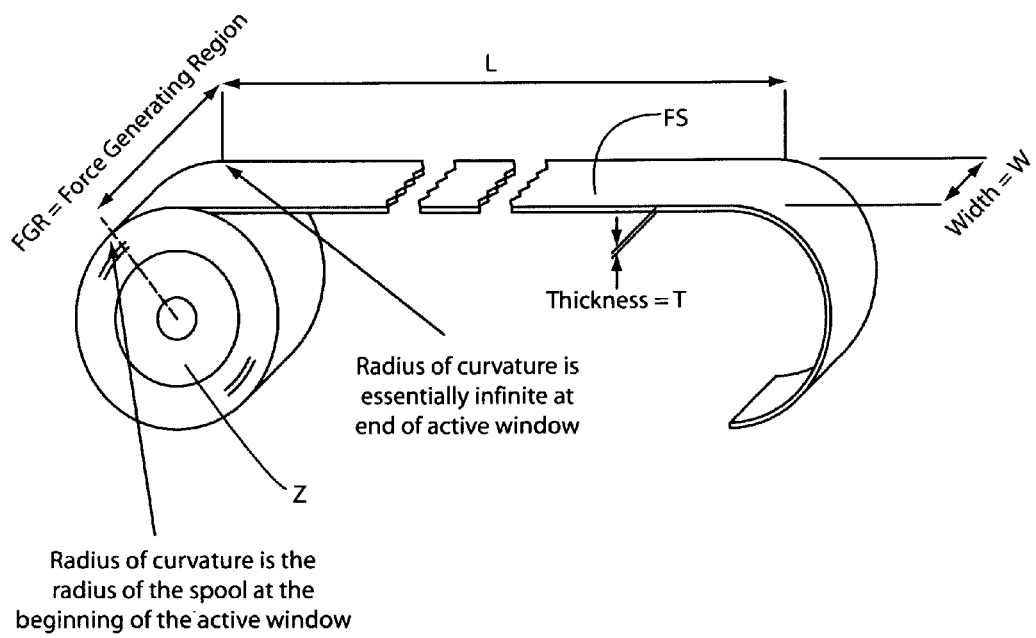
FIG. 11 is a generally perspective view of the prior art retractable spring shown in FIG. 10 as it appears in a partially expanded configuration.

The prior art Negator extension spring comprises a prestressed flat strip "FS" of spring material that is formed into virtually constant radius coils around itself or on a drum "Z" having a radius R-1 (FIG. 11). The area identified in FIG. 11 of the drawings as "FGR" designates the "active region" or "the force generating region" of the constant for spring. It should be understood that in this "active region" the radius of curvature of the spring changes and it is this change in radius of curvature of the spring that is responsible for the generation of the force. In fact, the radius of curvature changes from essentially infinity to a value equal to the radius R-1 of the spool on which the spring is wound. As will be discussed in greater detail hereinafter, increasing the mass of material in this "force generating region" will increase the force provided by the spring. Conversely, decreasing the mass of material in the "force generating region" will result in a reduction of the force generated by the spring. The mass in the active region can be changed by changing the thickness of the spring, the width of the spring, the density of material of the spring, or any combination of these. It should be further noted that because the force generating region takes up some portion of the length of the spring it will tend to average any point-by-point changes in physical or structural properties of the spring. The variable L shown in FIG. 11 of the drawings is defined to be the distance from the force generating region to the end of the spring. When deflected, the spring material straightens as it leaves the drum (see FIG. 11). This straightened length of spring actually stores the spring's energy through its tendency to assume its natural radius.

The force delivered by a typical prior art constant force spring, such as the Negator extension spring depends on several structural and geometric factors. Structural factors include material composition and heat treatment. Geometric factors include the thickness of the spring "T", the change in radius of curvature of the spring as the spring is extended, and the width "W" of the spring.

Figure 12:
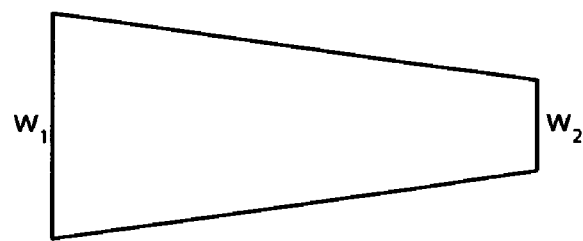
FIG. 12 is a generally illustrative view of the configuration of a retractable spring that would deliver a force that decreases by a factor of $w_3/w_2$ as a spring returned from its fully extended configuration to its fully coiled configuration.
Figure 13:
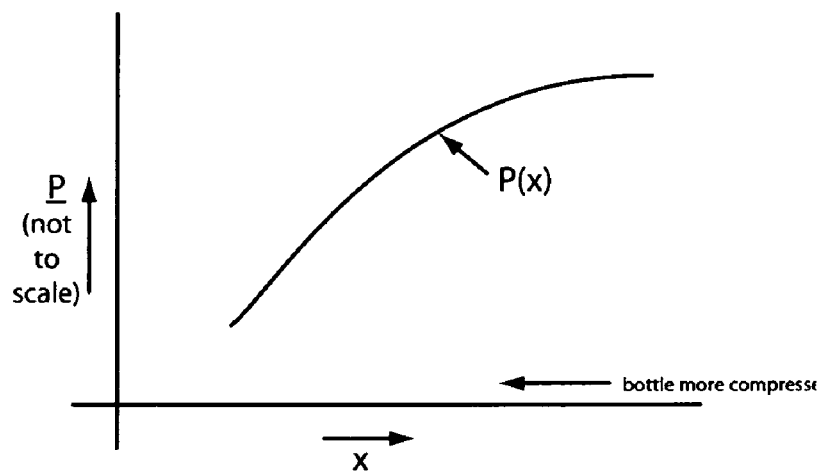
FIG. 13 is a generally graphical representation plotting pressure versus the length of the reservoir container when a constant force spring is used to compress a bellows-like reservoir container.

Turning now to a consideration of the novel variable force springs of the present invention, these springs can be constructed from various materials, such as metal, plastic, ceramic, composite and alloys, that is, intermetallic phases, intermetallic compounds, solid solution, metal-semi metal solutions including but not limited to Al/Cu, Al/Mn, Al/Si, Al/Mg, Al/Mg/Si, Al/Zn, Pb/Sn/Sb, Sn/Sb/Cu, Al/Sb, Zn/Sb, In/Sb, Sb/Pb, Au/Cu, Ti/Al/Sn, Nb/Zr, Cr/Fe, non-ferrous alloys, Cu/Mn/Ni, Al/Ni/Co, Ni/Cu/Zn, Ni/Cr, Ni/Cu/Mn, Cu/Zn, Ni/Cu/Sn. These springs comprise a novel modification of the prior art constant force springs to provide variable springs suitable for use in many diverse applications With the forgoing in mind, if one wanted to produce a spring that delivered a force that increased by a factor of two as the spring returned from its fully extended conformation to its equilibrium, or fully coiled conformation, one would require that, as illustrated in FIG. 12 of the drawings, the width of the spring change by a factor of two along its length. In the example illustrated in FIG. 13, the force will decrease by a factor of $w_1/w_2$ as the spring changes from a fully extended configuration to a fully retracted configuration.

With the forgoing in mind, one form of the modified spring of the present invention can be described algebraically as follows:

If x denotes the position of a point along a line that is parallel to the longitudinal axis of the spring and w(x) denotes the width of the spring at that point then:

$$w(x) = (\text{constant})x$$

This describes the case wherein the width varies linearly with x as is shown in FIG. 12 of the drawings.

However, it is to be observed that the relationship between a position along the longitudinal axis of the spring and the width of the spring at that position need not be linear as shown in FIG. 12. Further, the width of the spring could be any arbitrary function of x. Thus:

$$w(x) = f(x)$$

Where (x) denotes an arbitrary function of x.

Figure 14:
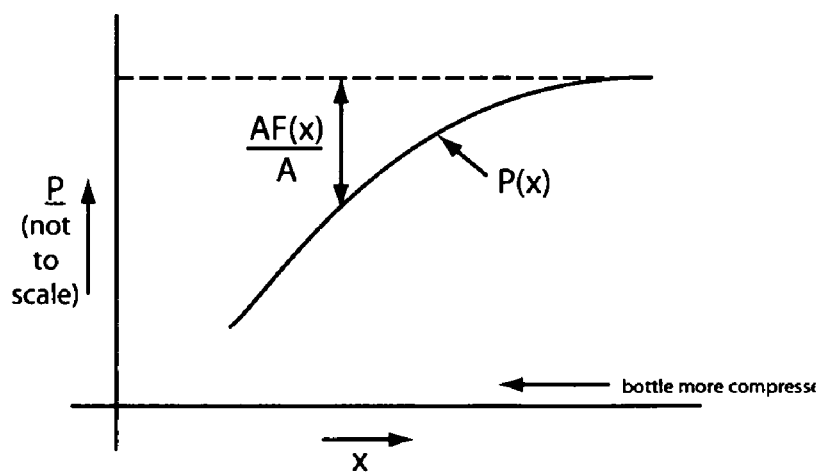
FIG. 14 is a generally graphical representation, similar to FIG. 13, plotting pressure versus the degree of compression for the reservoir container when the container is compressed by a constant force spring.

Using this concept a spring can be designed that can be used to controllably compress a bellows type reservoir, such as reservoir 35, which when compressed by the modified spring exhibits a pressure vs. degree of compression curve of the character shown in FIG. 14. Stated another way, it is apparent that the concept can be employed to design a spring that generates a pressure that is independent of the degree of compression of the bellows-type reservoir.

By way of example, suppose that the pressure vs. degree of compression curve for a bellows-like container when compressed by a constant force spring is exemplified by the curve P(x) and the force of the constant force spring is identified as "FCFS". Further assume that the drop in pressure as the container is compressed is due to the force "BF(x)", which is the force required to compress the container. Then the net force producing the pressure in the container can then be written:

$$F(x) = \text{FCFS} - \text{BF}(x)$$

Assume for simplicity that the area on which the force F acts is constant and is represented by "A". Then the pressure in the bottle is:

$$P(x) = (\text{FCFS} - \text{BF}(x))/A$$

This equation describes, in functional form, the curve labeled P(x) in FIG. 14, and includes explicitly the contributions of the two forces generating the pressure within the reservoir 35 of the bellows-like container, that is the force due to the spring and the force due to the bellows-like container.

The forgoing analysis allows one to design a spring, the force of which changes in such a way that the sum of all forces generating the pressure in the container is independent of the degree of the compression of the container, i.e., independent of the variable x. The force delivered by such a spring can be stated as:

$$F_{ms}(x) = \text{FCFS} + \text{AF}(x)$$

Where "FCFS" is the force delivered by the original constant force spring and AF(x) is an additional force whose functional form is to be determined. Thus, the modified spring can be thought of as being composed of two parts, one part delivers the force of the original constant force spring (a force independent of x) and the other delivers a force that depends on the variable x.

For this system the net force generating the pressure in the reservoir of the bellows-like container is stated as:

$$FS(x) = F_{ms}(x) - \text{BF}(x) = \text{FCFS} + \text{AF}(x) - \text{BF}(x)$$

Assuming that:

$$\text{AF}(x) = \text{BF}(x) \text{ for all } x.$$

Then the total force compressing the container is:

$$FS(x) = \text{FCFS} + \text{AF}(x) - \text{AF}(x) = \text{FCFS}$$

which force is independent of the degree of compression of the container, and wherein the pressure within the container is independent of the degree of compression of the container.

$$P_{ms}(x) = (\text{FCFS} + \text{AF}(x) - \text{AF}(x))/A = \text{FCFS}/A$$

Where $P_{ms}(x)$ denotes the pressure in the fluid reservoir when the modified spring of the invention is used.

In designing the modified spring of the present invention, the information contained in the pressure vs. displacement curve when the container is compressed by a constant force spring can be used to determine how the cross-sectional mass, in this case the width of the spring, must vary as a function of x in order that the pressure in the container when compressed with the modified spring remains constant.

The force delivered by the spring being linearly dependent on the width of the spring if all other things remain constant, thus:

$$\text{AF}(x) = (\text{constant})w(x)$$

Substituting this into equation:

$$P(x) = (\text{FCFS} - \text{BF}(x))/A, \text{ then:}$$

$$P(x) = (\text{FCFS} - \text{AF}(x))/A = (\text{FCFS} - \text{constant})w(x))/A$$

However, it is to be observed that FCFS/A−P(x) is just the difference between the two curves shown in FIG. 14, FCFS/A being the horizontal line. Thus, the modification to the width, denoted w(x), of the original constant force spring is proportional to the difference between the two curves shown in FIG. 14. In other words, the shape of the change in the width of the spring as a function of x is similar to the difference between the two curves as a function of x. Furthermore, one can simply "read off" the shape of the curve w(x) from the pressure vs. displacement curve.

The broader utility of a variable force spring, whose width defines the specific force, may be that the spring design can be appropriately constructed to deliver a non-linear and highly variable force to meet a specific requirement. In this way, a spring that has a width that simply decreases as it is unrolled could be used. Alternatively, the spring could have an increasing width, followed by a width that decreases again during its distention. The spring force provided is therefore highly tunable to meet a variety of applications and requirements, simply by constructing a spring of specific width at the desired distension. Although a virtually infinite number of designs are possible, by way of non-limiting example, several differently configured springs are illustrated in FIGS. 15 through 30 of the drawings.

Figure 15:
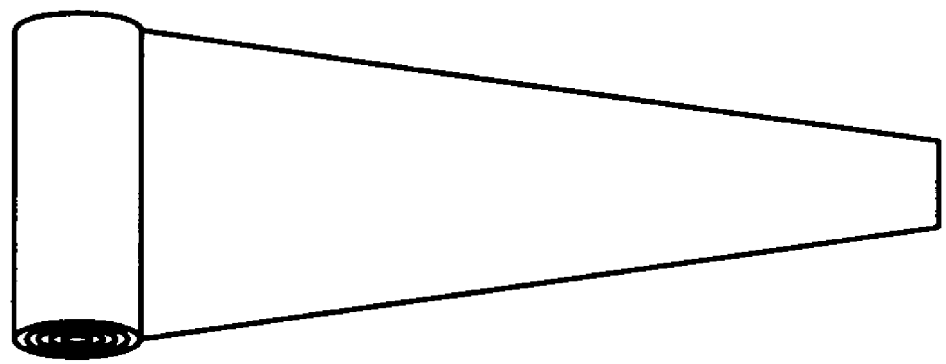
FIG. 15 is a generally illustrative view of the retractable spring of a first modified configuration.
Figure 15A:
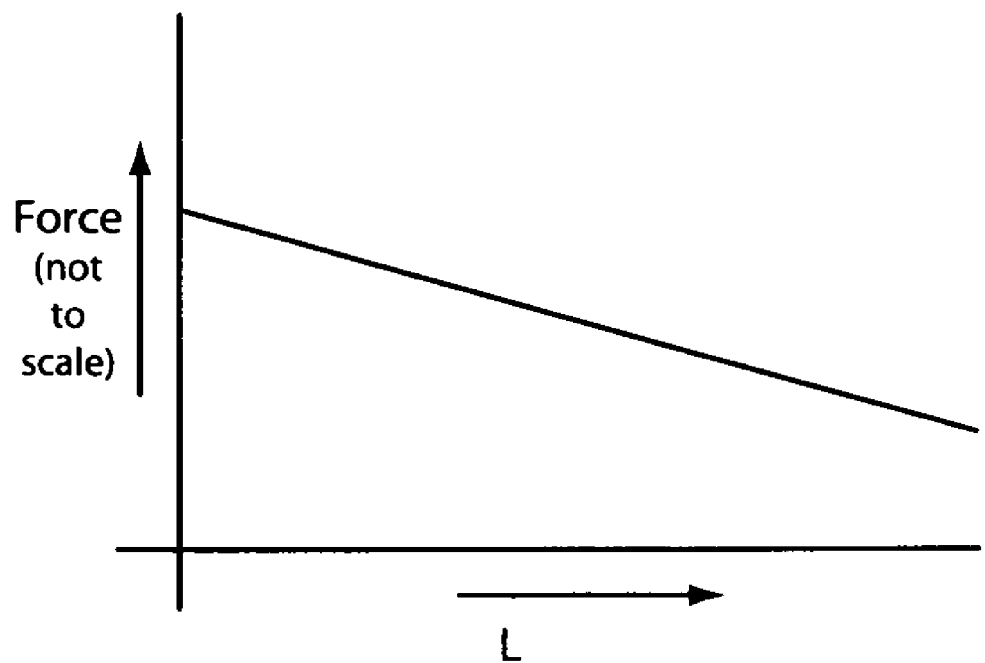
FIG. 15A is a generally graphical representation plotting force exerted by the spring shown in FIG. 15 versus position along the length of the spring.
Figure 16:
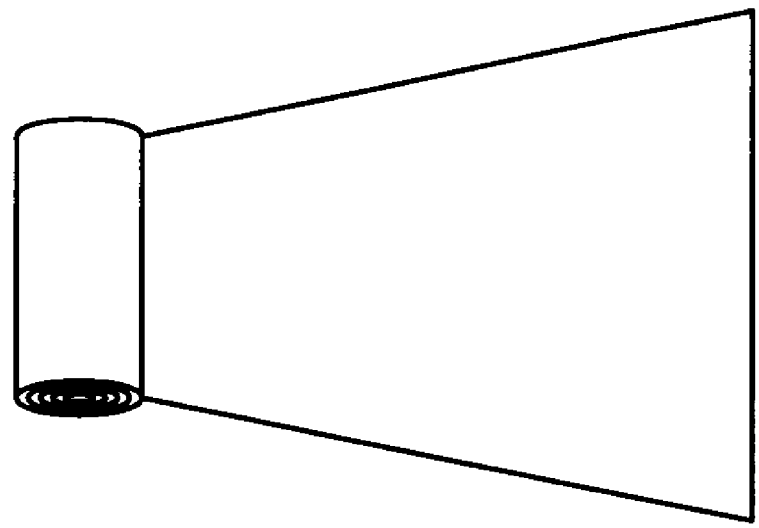
FIG. 16 is a generally illustrative view of the retractable spring of a second modified configuration.
Figure 16A:
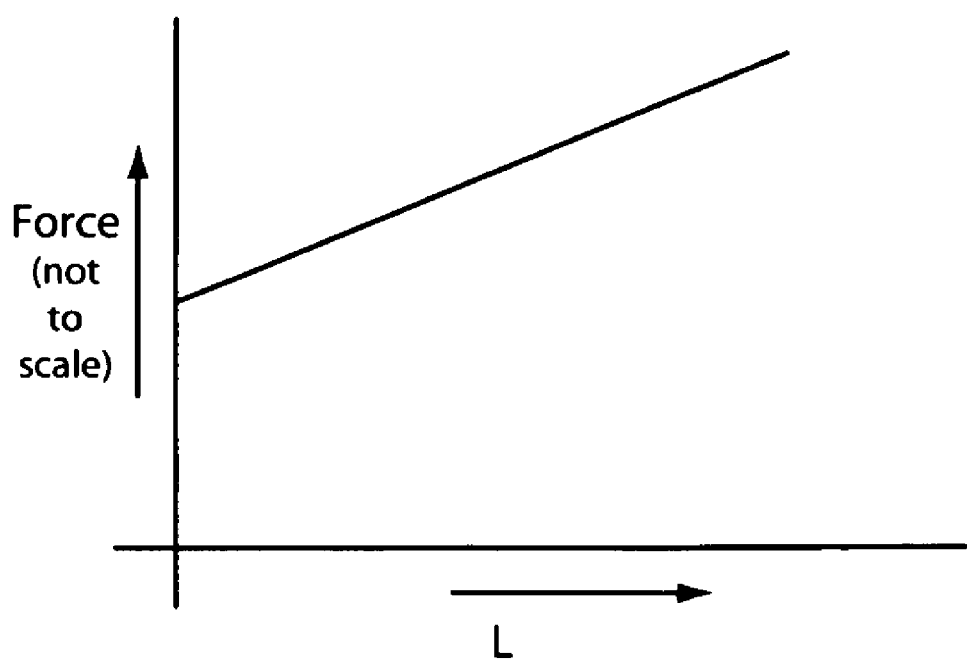
FIG. 16A is a generally graphical representation plotting force exerted by the spring shown in FIG. 16 versus position along the length of the spring.

Referring to FIG. 15 of the drawings one form of variable force spring having varying cross-sectional mass along its length is there illustrated. In this instance, the varying cross-sectional mass is achieved by a constant force spring that has been modified to exhibit varying width along its length. As shown in FIG. 15A, which is a plot of Force versus "L", where "L" is the distance from the force generating region of the spring to the end of the spring, the spring provides a decreasing force as it is retracted. Conversely, the spring depicted in FIG. 16 of the drawings, which also achieves varying cross-sectional mass by a spring exhibiting varying width along its length, provides a greater force as it retracts (see FIG. 16A).

Figure 17:
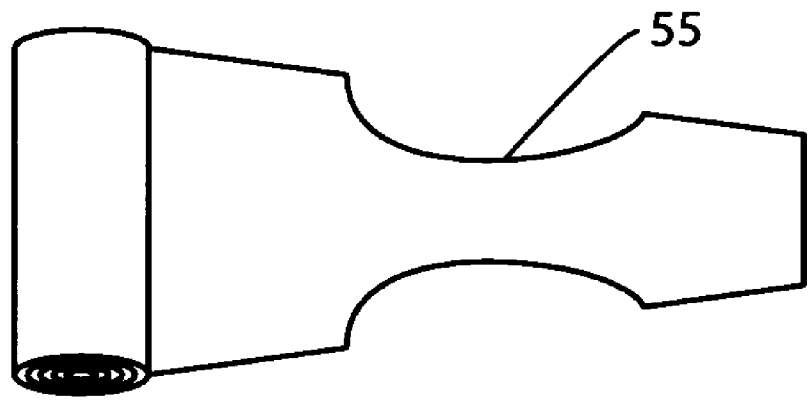
FIG. 17 is a generally illustrative view of the retractable spring of a third modified configuration.
Figure 17A:
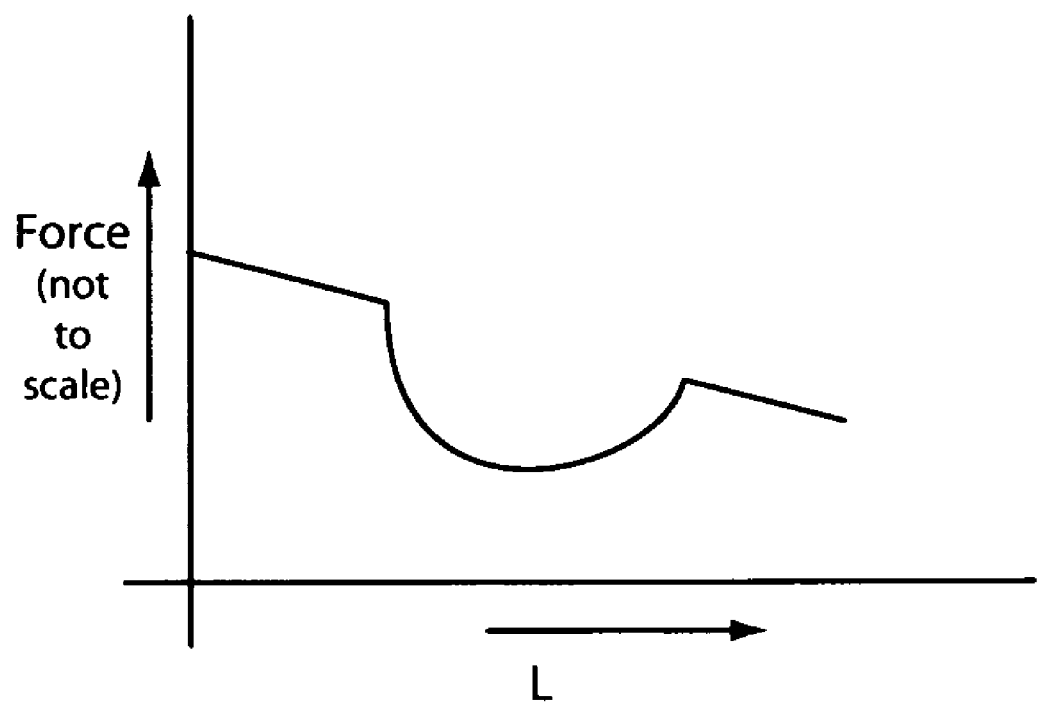
FIG. 17A is a generally graphical representation plotting force exerted by the spring shown in FIG. 17 versus position along the length of the spring.

With regard to the spring depicted in FIG. 17, this spring achieves varying cross-sectional mass by a constant force spring that has been modified to exhibit varying width along its length and also to exhibit at least one area of reduced width along its length. As illustrated in FIG. 17A of the drawings, as this spring rolls up from the extended position shown in FIG. 17, it will provide gradually less force, followed by a non-linear reduction in force at the area designated in FIG. 17 as 55, followed again by a non-linear increase in force, and finally at the point at which it is almost completely retracted, exhibits a gradually decreasing force.

Figure 18:
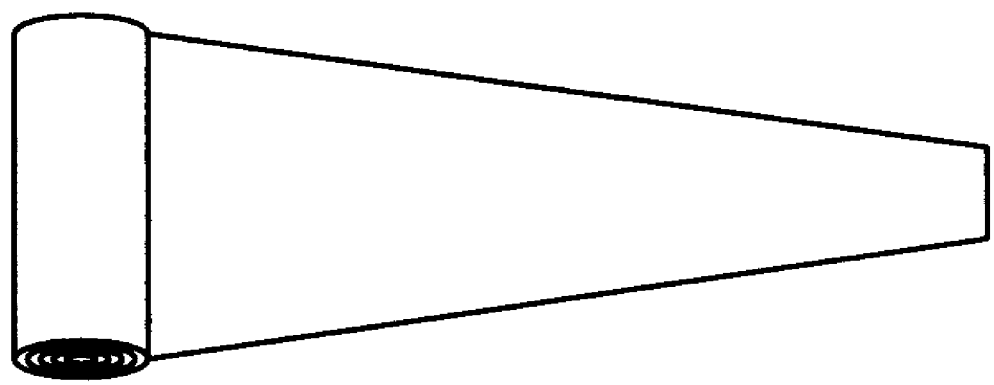
FIG. 18 is a generally illustrative view of the retractable spring of a fourth modified configuration.
Figure 18A:
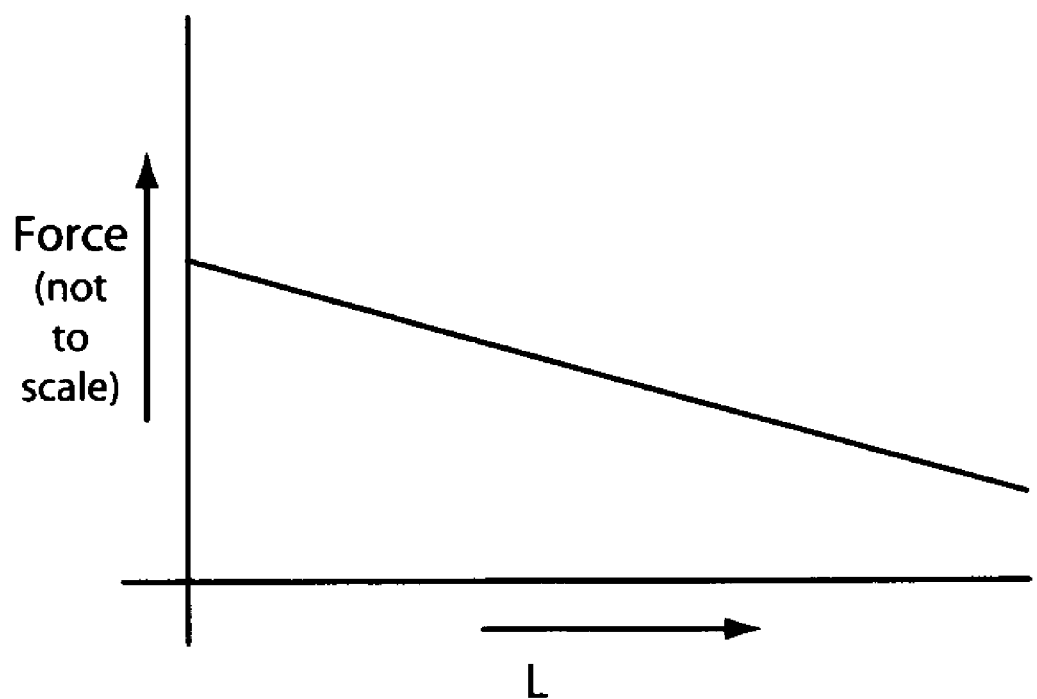
FIG. 18A is a generally graphical representation plotting force exerted by the spring shown in FIG. 18 versus position along the length of the spring.

FIG. 18 is a generally illustrative view of the retractable spring of a modified configuration somewhat similar to that shown in FIG. 15 of the drawings. In this latest spring configuration the varying cross-sectional mass is once again achieved by a constant force spring that has been modified to exhibit varying width along its length. As illustrated in FIG. 18A, which is a generally graphical representation plotting force exerted by the spring shown in FIG. 18 versus "L", the spring provides a decreasing force as it is retracted.

Figure 19:
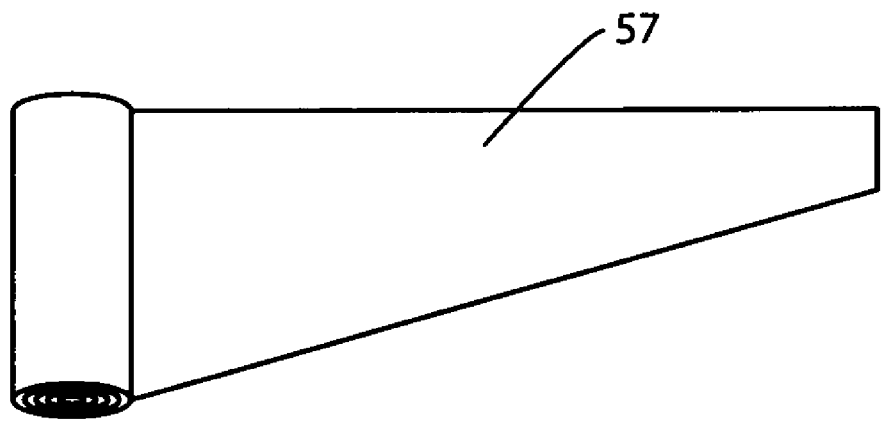
FIG. 19 is a generally illustrative view of the retractable spring of a fifth modified configuration.
Figure 19A:
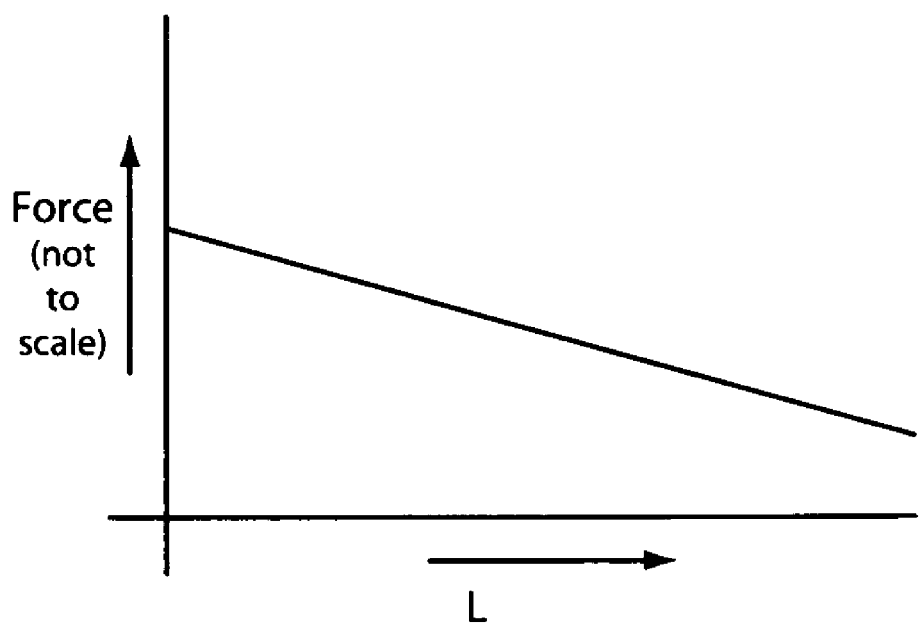
FIG. 19A is a generally graphical representation plotting force exerted by the spring shown in FIG. 19 versus position along the length of the spring.

FIG. 19 is a generally illustrative view of still another form of retractable spring wherein the varying cross-sectional mass is achieved by a constant force spring that has been modified to exhibit varying width along its length. More particularly, this latest form of the modified spring exhibits a tapered body portion 57. As illustrated in FIG. 19A, which is a generally graphical representation plotting force exerted by the spring shown in FIG. 19 versus "L", that is the distance from the force generating region of the spring to the end of the spring., the spring provides a decreasing force as it is retracted.

Figure 20:
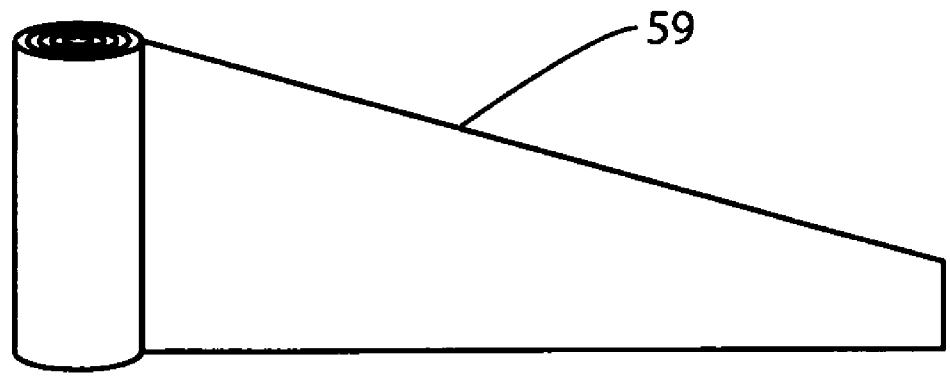
FIG. 20 is a generally illustrative view of the retractable spring of a sixth modified configuration.
Figure 20A:
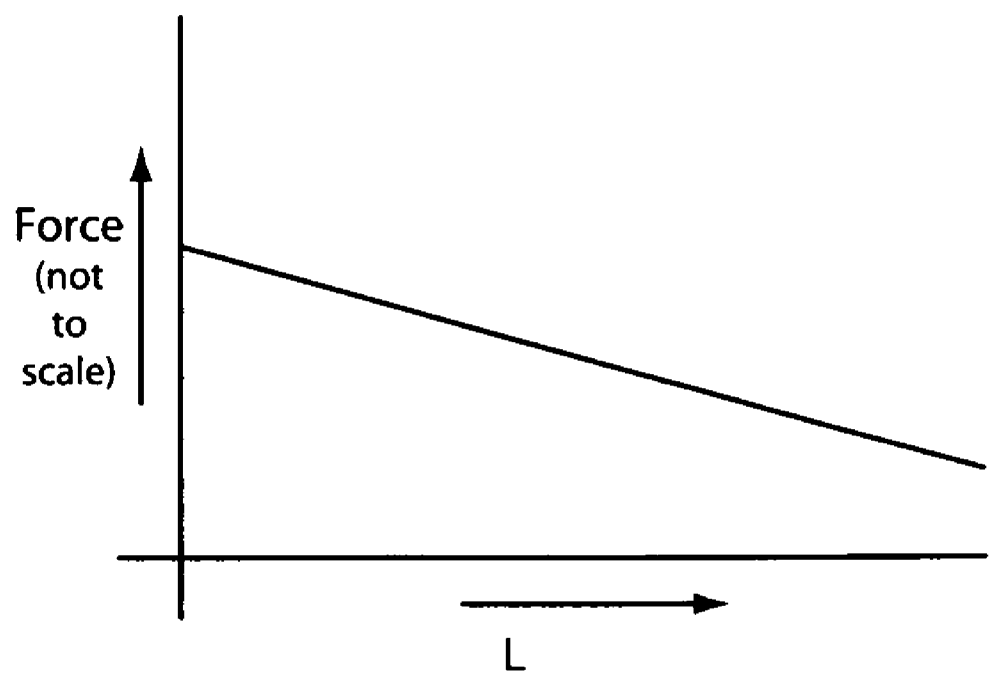
FIG. 20A is a generally graphical representation plotting force exerted by the spring shown in FIG. 20 versus position along the length of the spring.

FIG. 20 is a generally illustrative view of the yet another form of retractable spring wherein the varying cross-sectional mass is achieved by a constant force spring that has been modified to exhibit varying width along its length. More particularly, this latest form of the modified spring exhibits a tapered body portion 59, which unlike the body portion 57 of the spring shown in FIG. 19 tapers downwardly rather than upwardly. As illustrated in FIG. 20A, which is a generally graphical representation plotting force exerted by the spring shown in FIG. 20 versus "L", the spring provides a decreasing force as it is retracted.

Figure 21:
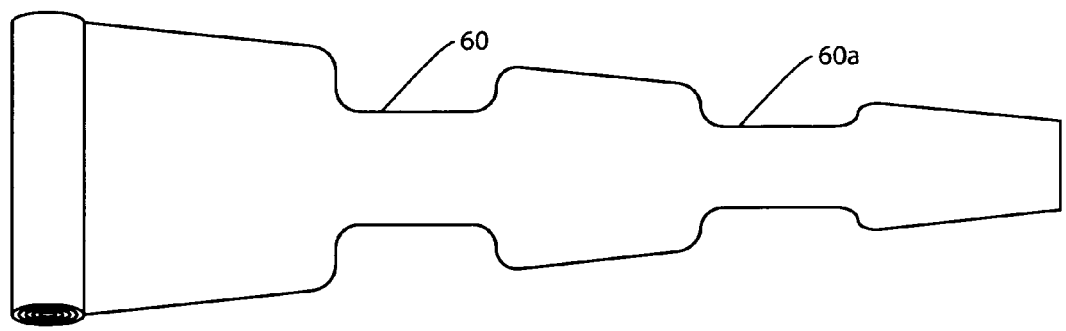
FIG. 21 is a generally illustrative view of the retractable spring of a seventh modified configuration.
Figure 21A:
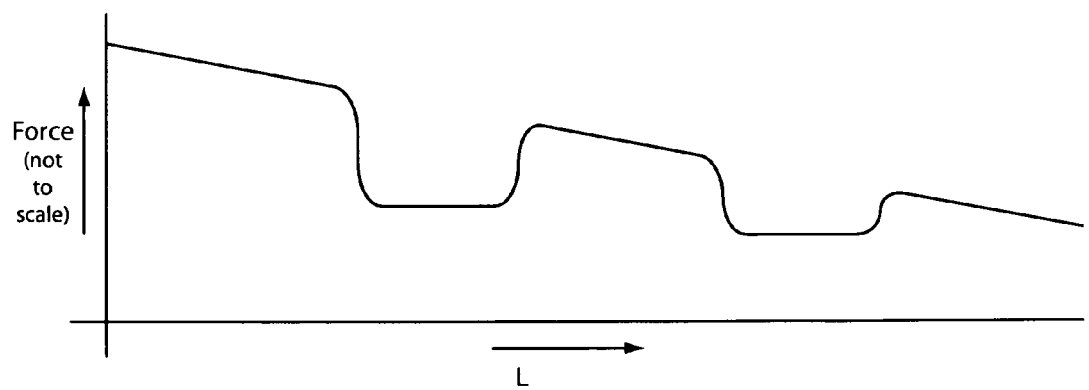
FIG. 21A is a generally graphical representation plotting force exerted by the spring shown in FIG. 21 versus position along the length of the spring.

With regard to the spring depicted in FIG. 21, this spring, which is somewhat similar to the spring configuration shown in FIG. 17 of the drawings, achieves varying cross-sectional mass by a constant force spring that has been modified to exhibit varying width along its length and also to exhibit a plurality of areas of reduced width along its length. As illustrated in FIG. 21A of the drawings, as this spring rolls up from the extended position shown in FIG. 21, it will provide gradually less force, followed by a non-linear reduction in force at the area designated in FIG. 21 as 60, followed again by a non-linear increase in force, followed by a non-linear reduction in force at the area designated in FIG. 21 as 60a and finally at the point at which it is almost completely retracted, once again exhibits a gradually decreasing force.

Figure 22:
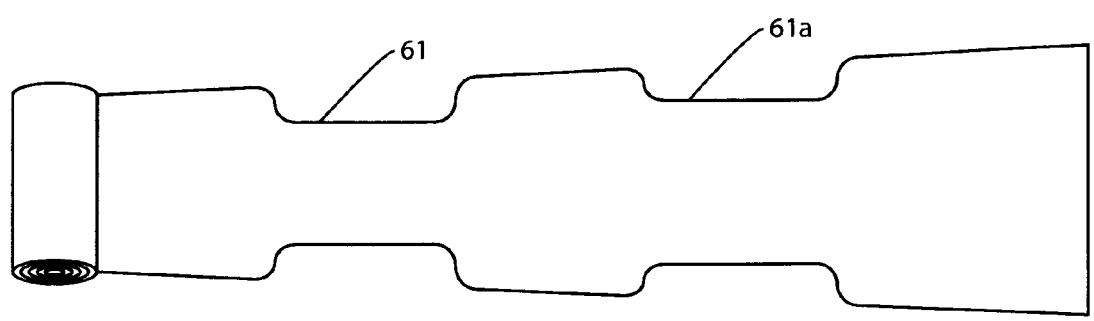
FIG. 22 is a generally illustrative view of the retractable spring of an eighth modified configuration.
Figure 22A:
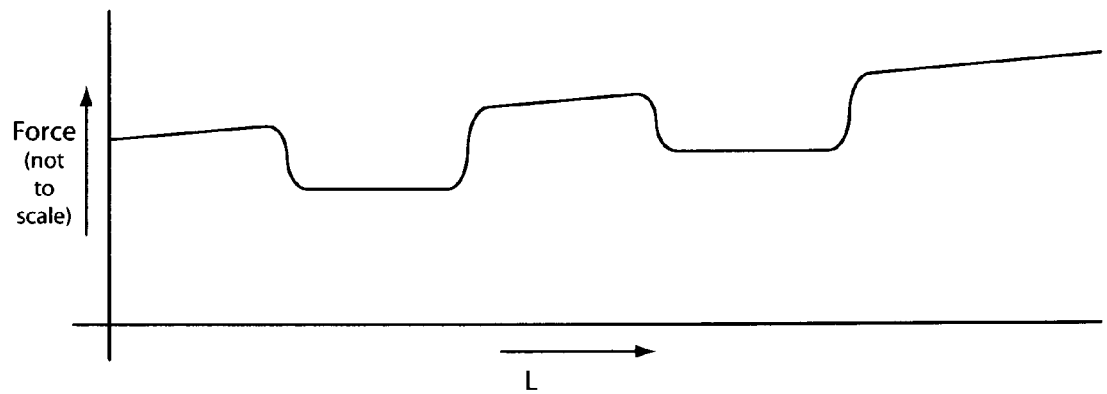
FIG. 22A is a generally graphical representation plotting force exerted by the spring shown in FIG. 22 versus position along the length of the spring.

Referring next to FIG. 22 of the drawings, the spring there depicted, which is somewhat similar to the spring configuration shown in FIG. 21 of the drawings, achieves varying cross-sectional mass by a constant force spring that has also been modified to exhibit varying width along its length and also to exhibit a plurality of areas of reduced width along its length. However, as illustrated in FIG. 22A of the drawings, as this spring rolls up from the extended position shown in FIG. 22, it will provide gradually increased force, followed by a non-linear decrease in force at the area designated in FIG. 22 as 61, followed again by a non-linear increase in force, followed by a non-linear decrease in force at the area designated in FIG. 22 as 61a and finally at the point at which it is almost completely retracted, once again exhibits a gradually increasing force.

Figure 23:
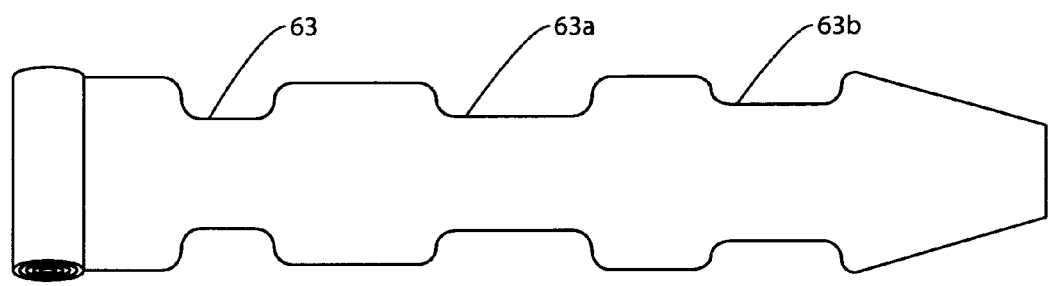
FIG. 23 is a generally illustrative view of the retractable spring of a ninth modified configuration.
Figure 23A:
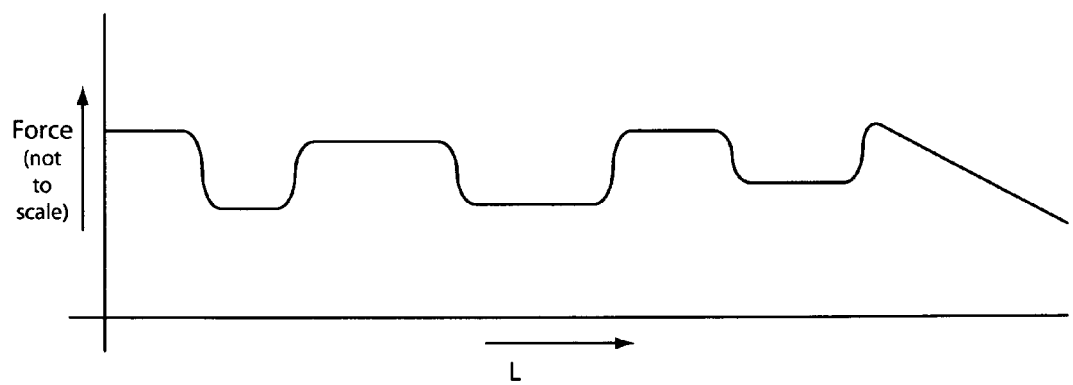
FIG. 23A is a generally graphical representation plotting force exerted by the spring shown in FIG. 23 versus position along the length of the spring.

Turning next to FIG. 23 of the drawings, the spring there depicted is also somewhat similar to the spring configuration shown in FIG. 21 of the drawings. However, the spring shown in FIG. 23 does not exhibit a tapered body portion like that of the spring illustrated in FIG. 21. Rather, the spring achieves varying cross-sectional mass by a constant force spring that has also been modified only to exhibit a plurality of areas of reduced width along its length. As illustrated in FIG. 23A of the drawings, as this spring rolls up from the extended position shown in FIG. 23, it will provide a slightly decreased force, followed by a non-linear decrease in force at the area designated in FIG. 23 as 63, followed again by a non-linear increase in force, followed by a non-linear decrease in force at the area designated in FIG. 23 as 63a, followed again by a non-linear increase in force, followed by a non-linear decrease in force at the area designated in FIG. 23 as 63b and finally at the point at which it is almost completely retracted, once again exhibits a gradually decreasing force.

Figure 24:
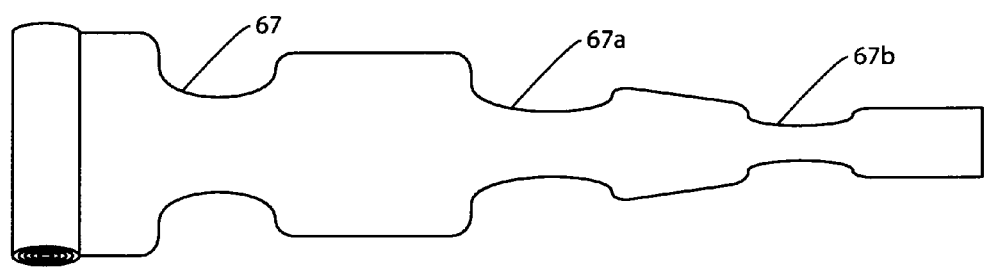
FIG. 24 is a generally illustrative view of the retractable spring of a tenth modified configuration.
Figure 24A:
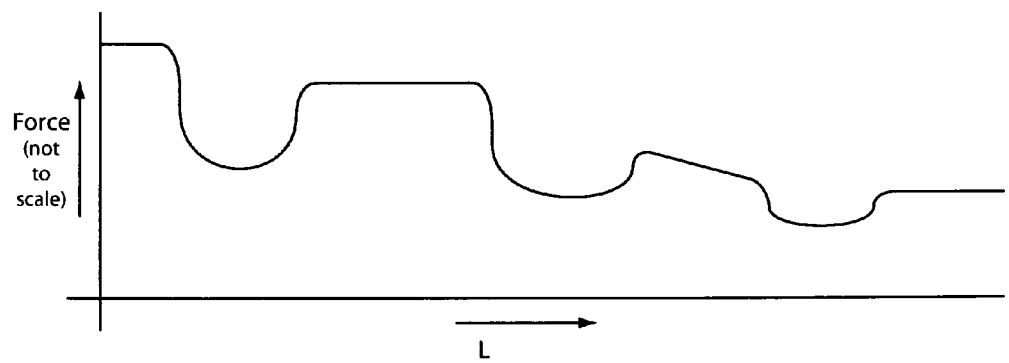
FIG. 24A is a generally graphical representation plotting force exerted by the spring shown in FIG. 24 versus position along the length of the spring.

Referring now to FIG. 24 of the drawings, the spring there depicted, is also somewhat similar to the spring configuration shown in FIG. 21 of the drawings. However, the spring shown in FIG. 24 exhibits both a non-tapered body portion such as that of the spring shown in FIG. 23 and also exhibits a tapered body portion like that of the spring illustrated in FIG. 21. In this instance, the spring achieves varying cross-sectional mass by a constant force spring that has been modified to exhibit a reduced width along its length and has also been modified to exhibit a plurality of areas of reduced width along its length. As illustrated in FIG. 24A of the drawings, as this spring rolls up from the extended position shown in FIG. 24, it will provide a generally linear force, followed by a non-linear decrease in force at the area designated in FIG. 24 as 67, followed again by a non-linear increase in force, followed by a generally linear force, followed by a non-linear decrease in force at the area designated in FIG. 24 as 67a, followed again by a non-linear increase in force, followed by a non-linear decrease in force at the area designated in FIG. 24 as 67b and finally at the point at which it is almost completely retracted, once again exhibits a generally linear force.

Figure 25:
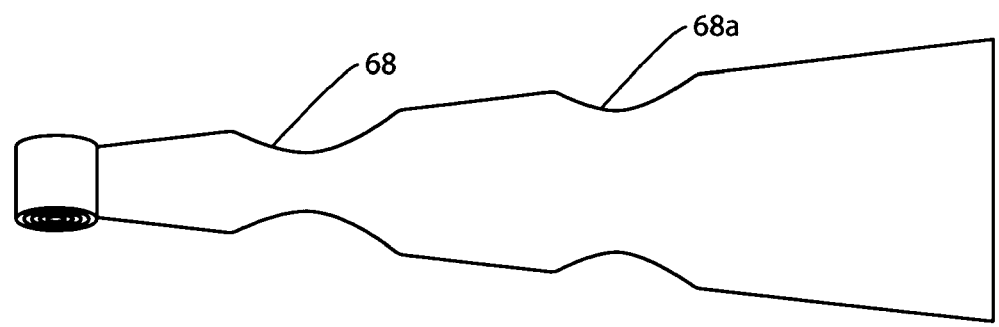
FIG. 25 is a generally illustrative view of the retractable spring of an eleventh modified configuration.
Figure 25A:
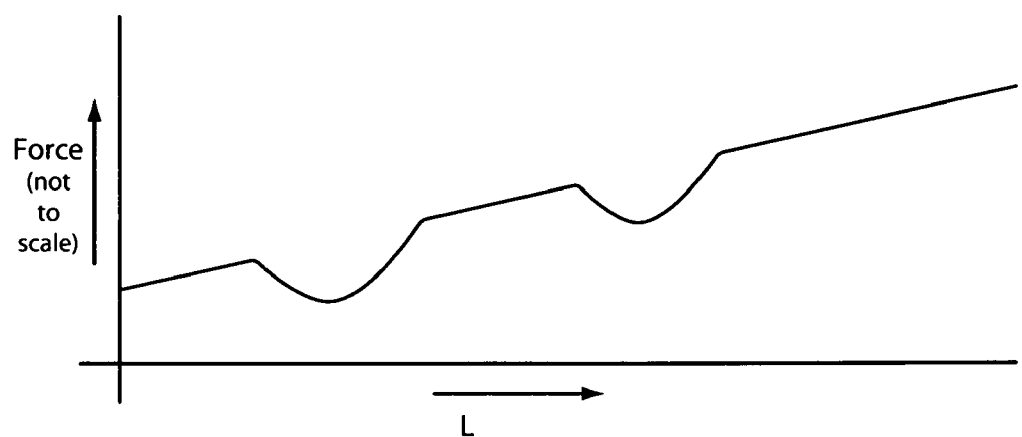
FIG. 25A is a generally graphical representation plotting force exerted by the spring shown in FIG. 25 versus position along the length of the spring.

Referring next to FIG. 25 of the drawings, the spring there depicted achieves varying cross-sectional mass by a constant force spring that has been modified to exhibit an increased width along its length and has also been modified to exhibit a plurality of areas of reduced width along its length. As illustrated in FIG. 25A of the drawings, as this spring rolls up from the extended position shown in FIG. 25, it will provide an increase in force, followed by a non-linear decrease in force at the area designated in FIG. 24 as 68, followed again by a non-linear increase in force, followed by a gradually increasing force, followed by a non-linear decrease in force at the area designated in FIG. 25 as 68a, followed by an increase in force and finally at the point at which it is almost completely retracted, once again exhibits a substantially increase in force.

Figure 26:
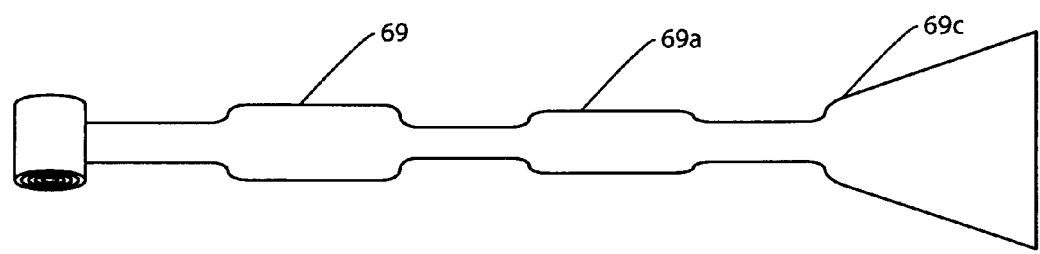
FIG. 26 is a generally illustrative view of the retractable spring of a twelfth modified configuration.
Figure 26A:
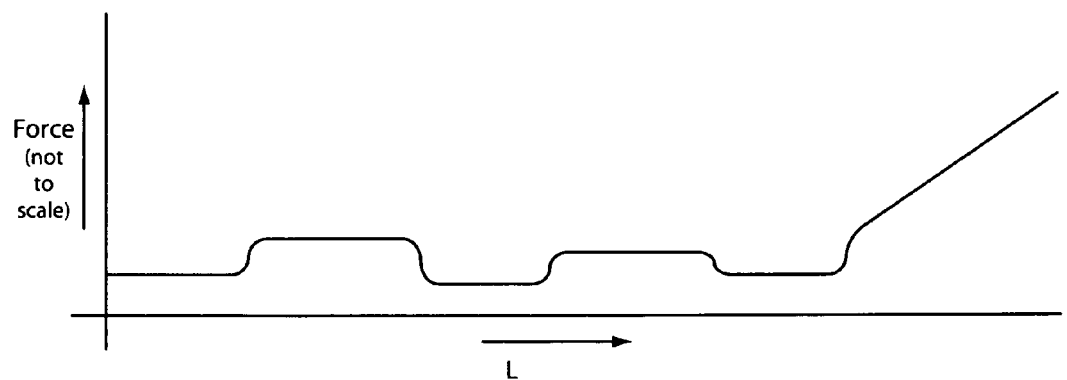
FIG. 26A is a generally graphical representation plotting force exerted by the spring shown in FIG. 26 versus position along the length of the spring.

Turning next to FIG. 26 of the drawings, the spring there depicted is somewhat similar to the spring configuration shown in FIG. 23 of the drawings and does not exhibit a tapered, central body portion like that of the spring illustrated in FIG. 21. Rather, the spring achieves varying cross-sectional mass by a constant force spring that has been modified in its central body portion to exhibit a plurality of areas of reduced width along its length and uniquely exhibits an outwardly tapered end portion. As illustrated in FIG. 26A of the drawings, as this spring rolls up from the extended position shown in FIG. 26, it will provide an increase in force at the area designated in FIG. 26 as 69, followed by a decrease in force, followed by an increase in force at the area designated in FIG. 26 as 69a, followed again by a decrease in force and finally at the point 69c at which it is almost completely retracted, will exhibit a gradually increasing force.

Figure 27:
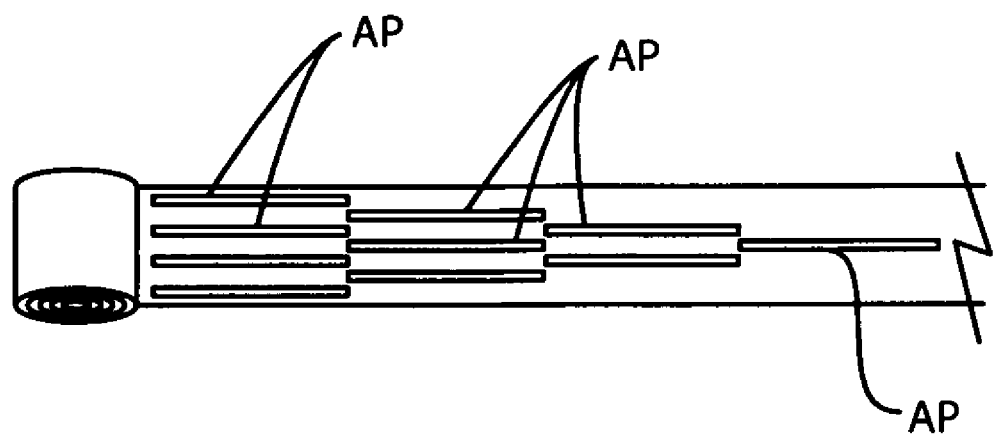
FIG. 27 is a generally illustrative view of the retractable spring of a thirteenth modified configuration.
Figure 27A:
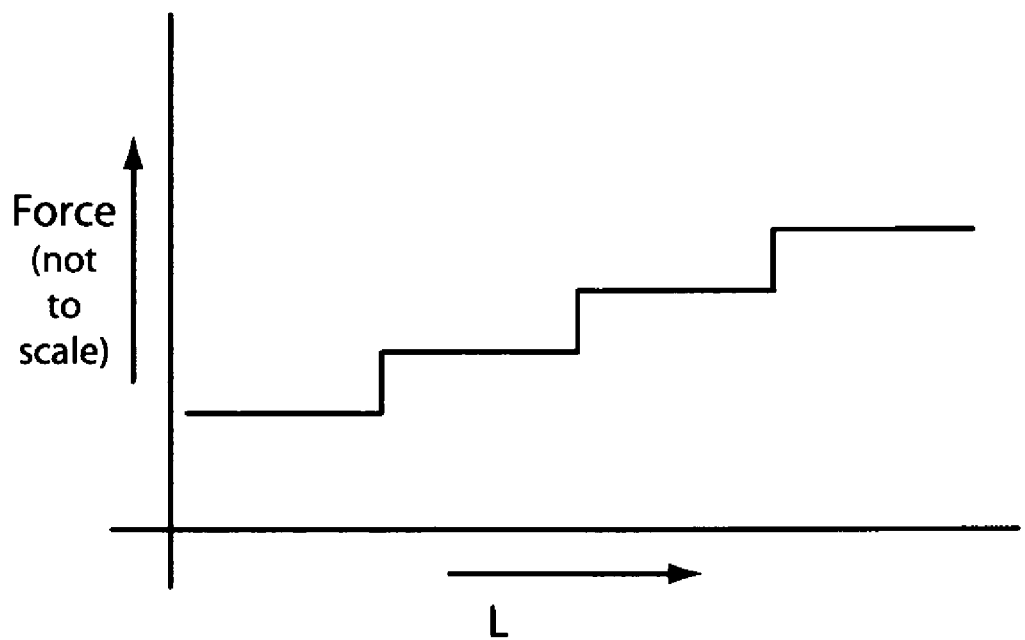
FIG. 27A is a generally graphical representation plotting force exerted by the spring shown in FIG. 27 versus position along the length of the spring.

Referring to FIG. 27 of the drawings still another form of variable force spring having varying cross-sectional mass along its length is there illustrated. In this instance, the varying cross-sectional mass is achieved by a constant force spring wherein the force generating region of the spring has been modified to include a plurality of spaced-apart apertures "AP" along its length. As shown in FIG. 27A, which is a schematic plot (not to scale) of force versus cross-sectional mass, the spring uniquely provides an increasing force in a stair step fashion as it is retracted. It is to be understood, that the apertures formed in the pre-stressed strip of spring material can be located in any desired configuration and can be both transversely and longitudinally spaced-apart to provide the desired force as the spring is retracted.

Figure 27B:
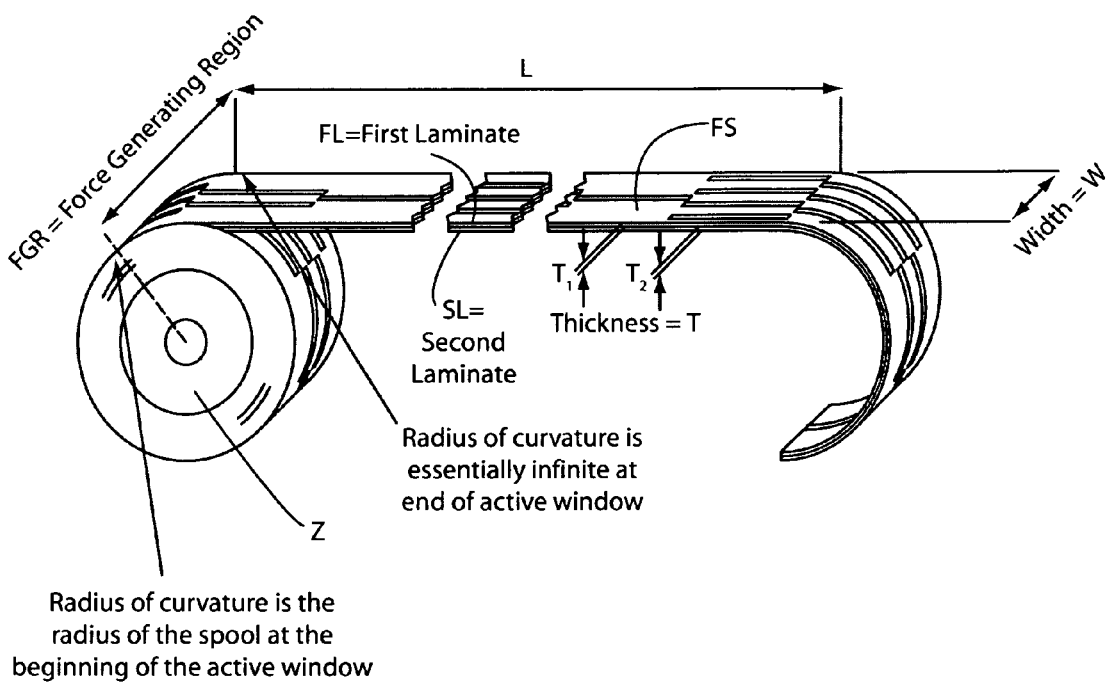
FIG. 27B is a generally perspective view of still another form of modified spring of the invention that here comprises a modification of the thirteenth modified spring configuration shown in FIG. 27 of the drawings.

FIG. 27B is a generally perspective view of still another form of the retractable spring of a modified configuration that is somewhat similar to that shown in FIG. 27 of the drawings. However, in this latest spring configuration the spring comprises a novel laminate construction made up of a first laminate FL and a second interconnected laminate SL. The varying cross-sectional mass is once again achieved by providing a plurality of the elongated transversely and longitudinally spaced-apart apertures, or slits.

Figure 28:
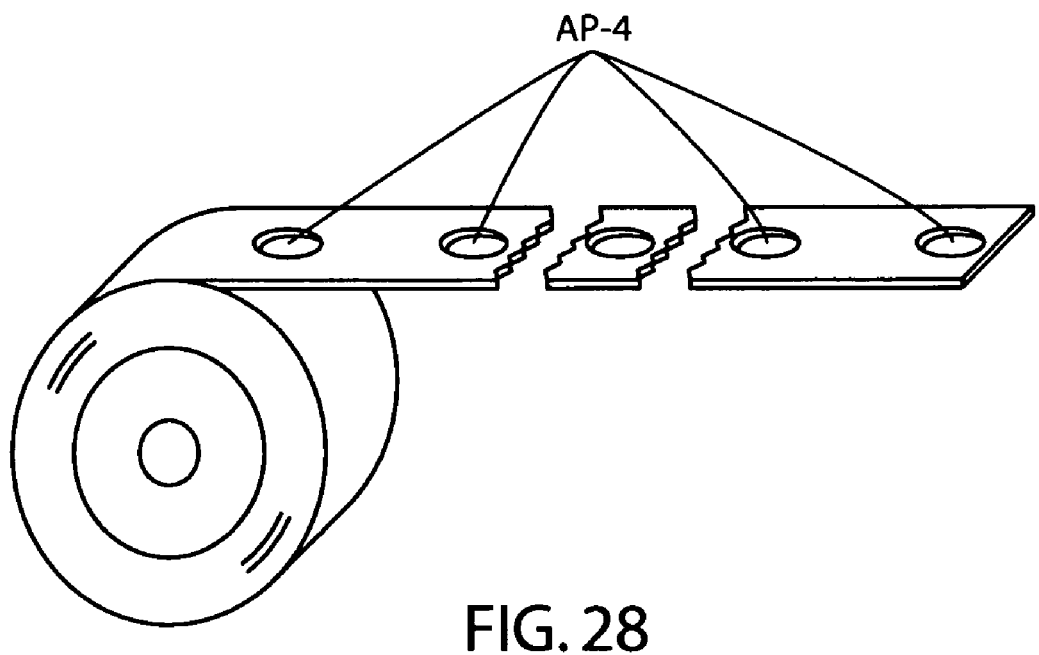
FIG. 28 is a generally illustrative view of the retractable spring of a fourteenth modified configuration.
Figure 28A:
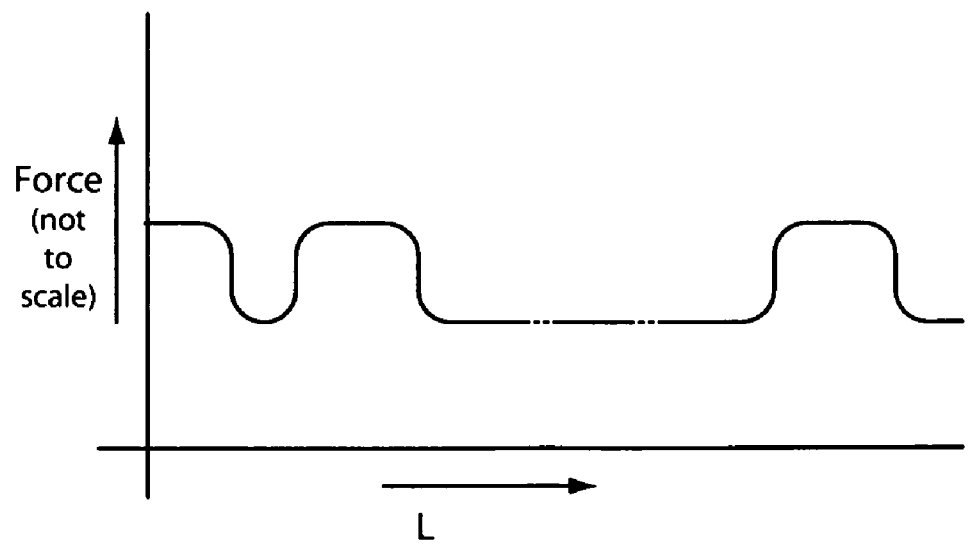
FIG. 28A is a generally graphical representation plotting force exerted by the spring shown in FIG. 28 versus position along the length of the spring.

Turning next to FIG. 28, still in other form of variable force spring having varying cross-sectional mass along its length is there illustrated. In this instance, the varying cross-sectional mass is once again achieved by a constant force spring wherein the force generating region of the spring has been modified to include a plurality of spaced-apart, generally circular shaped apertures "AP-4" along its length. As shown in FIG. 28A, which is a plot of force versus cross-sectional mass, the spring uniquely provides a decrease in force, followed by an increase in force, followed again by a lengthy decrease in force, followed by an increase in force and then followed by another decrease in force.

Figure 29:
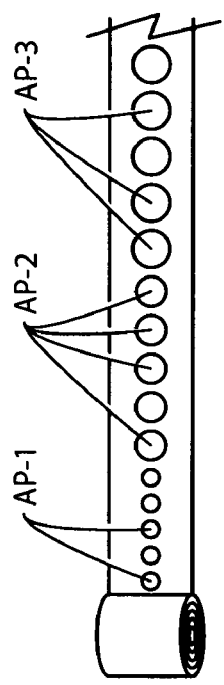
FIG. 29 is a generally illustrative view of the retractable spring of a fifteenth modified configuration.
Figure 29A:
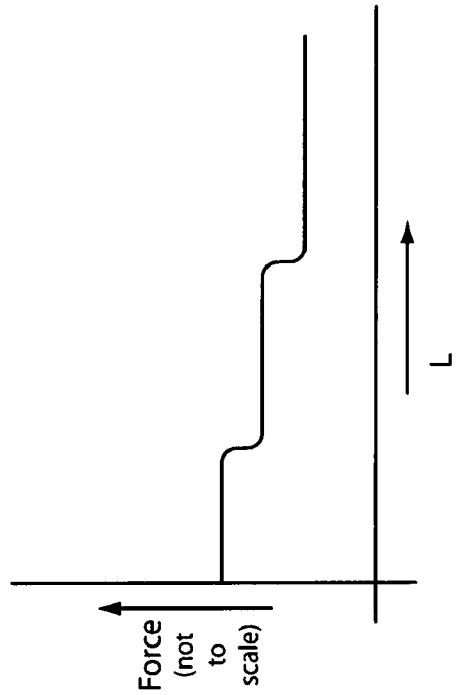
FIG. 29A is a generally graphical representation plotting force exerted by the spring shown in FIG. 29 versus position along the length of the spring.

Referring to FIG. 29, still in other form of variable force spring having varying cross-sectional mass along its length is there illustrated. In this instance, the varying cross-sectional mass is once again achieved by a constant force spring wherein the force generating region of the spring has been modified to include a plurality of spaced-apart, generally circular shaped apertures "AP-1", "AP-2" and "AP-3" along its length. As shown in FIG. 29A, which is a plot of force versus cross-sectional mass, the spring uniquely provides the desired variable decrease in force followed by the desired variable increase in force as it is retracted.

Figure 30:
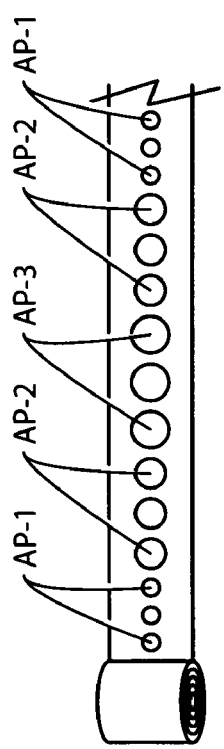
FIG. 30 is a generally illustrative view of the retractable spring of a sixteenth modified configuration.
Figure 30A:
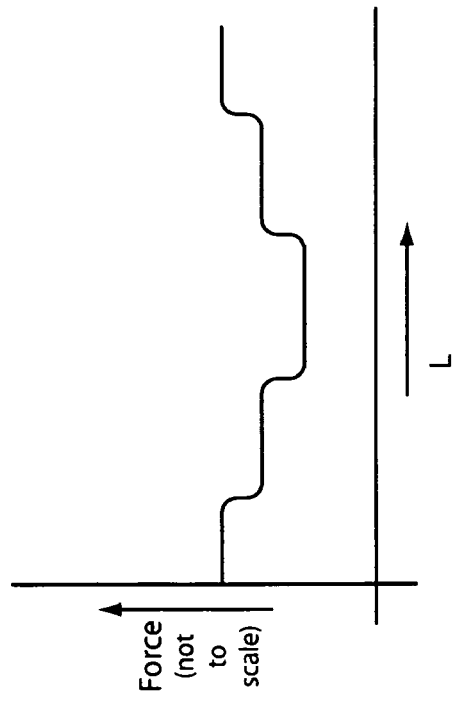
FIG. 30A is a generally graphical representation plotting force exerted by the spring shown in FIG. 30 versus position along the length of the spring.

Turning to FIG. 30, still in other form of variable force spring having varying cross-sectional mass along its length is there illustrated. In this instance, the varying cross-sectional mass is once again achieved by a constant force spring wherein the force generating region of the spring has been modified to include a plurality of spaced-apart, generally circular shaped apertures "AP-1", "AP-2", "AP-3" and "AP-4" along its length. As shown in FIG. 30A, which is a plot of force versus cross-sectional mass, the spring uniquely provides the desired variable decrease in force as it is retracted.

Referring to FIG. 31, still in other form of variable force spring having varying cross-sectional mass along its length is there illustrated. In this instance, the varying cross-sectional mass is once again achieved by a constant force spring wherein the force generating region of the spring has been modified to include a plurality of transversely and longitudinally spaced-apart, generally circular shaped apertures of increasing diameter in a direction away from the force generating region. As shown in FIG. 31A, which is a plot of force versus cross-sectional mass, the spring uniquely provides the desired variable decrease in force as it is retracted.

Referring to FIG. 32, still in other form of variable force spring having varying cross-sectional mass along its length is there illustrated. In this instance, the varying cross-sectional mass is once again achieved by a constant force spring wherein the force generating region of the spring has been modified to include a plurality of transversely and longitudinally spaced-apart, generally circular shaped apertures of decreasing diameter in a direction away from the force generating region. As shown in FIG. 32A, which is a plot of force versus cross-sectional mass, the spring uniquely provides the desired variable increase in force as it is retracted.

Considering further the operation of the device of the invention, with the apparatus in the configuration shown in FIG. 4, and with the fluid reservoir 35 filled with the medicament or diluent to be dispensed to the patient, the dispensing operation can be commenced by removing the top cover 77, which is snapped over a cover connector 77a that is provided on a connector member 79. With the cover removed as depicted in FIG. 5 of the drawings, the administration line 58a of the administration set 58 can be unwrapped from the guide sleeve 79a that extends from connector member 79 and about which it has been coiled (see FIG. 4). Removal of the top cover 77 also exposes selector member housing 80 that houses the important selector member 82 of the invention, the operation of which will presently be described.

To control the flow of medicinal fluid from reservoir 35 toward the administration set 58 of the invention and then on to the patient, flow control means are provided. This novel fluid flow control means, comprises two cooperating components, namely a rate control means for controlling the rate of fluid flow from the collapsible reservoir and an operating means for controlling fluid flow between the collapsible reservoir and the rate control means.

Considering first the operating means of the invention, it can be seen by referring to FIG. 4 of the drawings, selector member housing 80 carries a tear strip 84 which retains the selector member housing 80 in its first position and comprises the part of the operating means of the invention. When the tear strip is removed, a rotary force exerted on threaded selector member housing 80 will controllably move the housing along with the penetrating member 40a, which also comprises a part of the operating means of the invention, into the second penetrating position shown in FIG. 5. As the penetrating member moves into the second position, it will pierce the membrane 42 as well as the closure wall 39 in the manner shown in FIG. 5. Piercing of the membrane and the closure wall opens a fluid communication path from reservoir 35 to the rate control means of the invention via central fluid passageway 40b formed in penetrating member 40a.

Once the carriage locking means of the invention, which also comprises a part of the operating means of the invention, has been manipulated in the manner previously described to release the carriage 28, the carriage will move upwardly due to the urging of the variable force springs 48 and in so doing will collapse the container 34 in the manner shown in FIG. 5 of the drawings. As the container collapses, the fluid contained within reservoir 35 will flow outwardly of the reservoir through the outlet 36, into the passageway 40b of the piercing member 40a, through a filter 83 which is carried by the septum-penetrating assembly 40 and then onward toward the rate control assembly 84 of the rate of control means of the invention.

Considering in greater detail the important rate control means of the invention, this important means comprises a novel rate control assembly 84 the construction of which is the best seen in FIG. 31 of the drawings. Rate control assembly 84 here comprises a rate control plate 86 that is provided with circuitous fluid channels 86a, 86b, 86c, 86d, 86e and 86f, each of which is of a different geometry including channel length, depth, width and geometry. During the fluid delivery step, as the fluid flows from reservoir 35 into the inlet 86p of rate control plate via the orifice 88a of the rate control cover 88, each of the circuitous fluid channels will fill with the medicinal fluid to be dispensed to the patient. From the circuitous fluid channels, the fluid will flow into outlet passageways 90a, 90b, 90c, 90d, 90e, 90f and 90p respectively formed in rate control cover 90. From these outlet passageways, the fluid flows into and fills circumferentially spaced-apart fluid passageways 94a, 94b, 94c, 94d, 94e and 94f formed in selector housing 80 (see also FIG. 16B).

Figure 33:
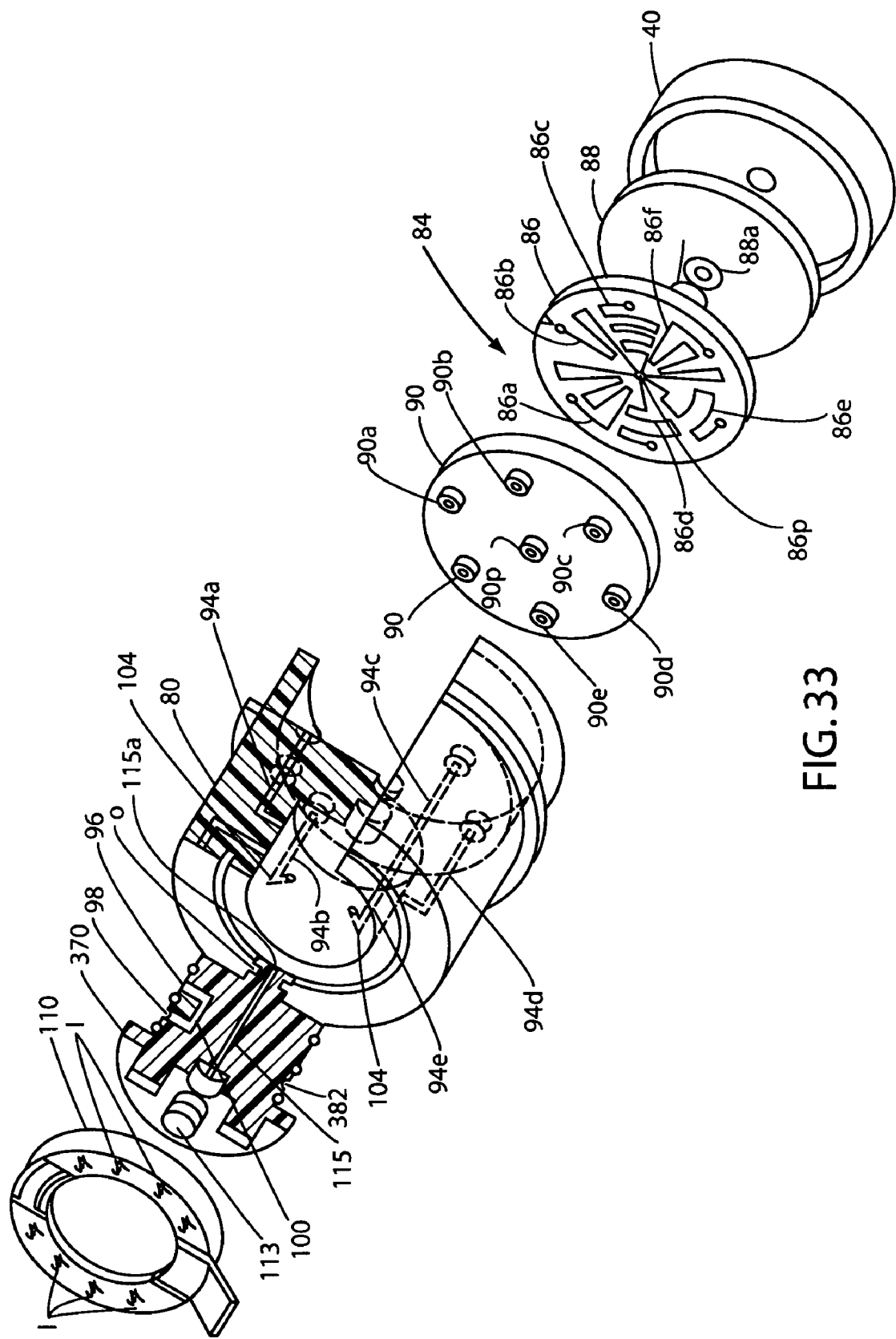
FIG. 33 is a generally perspective, exploded view of the upper portion of the fluid delivery device of the invention showing the construction of one form of the rate control of assembly of the device.
Figure 33A:
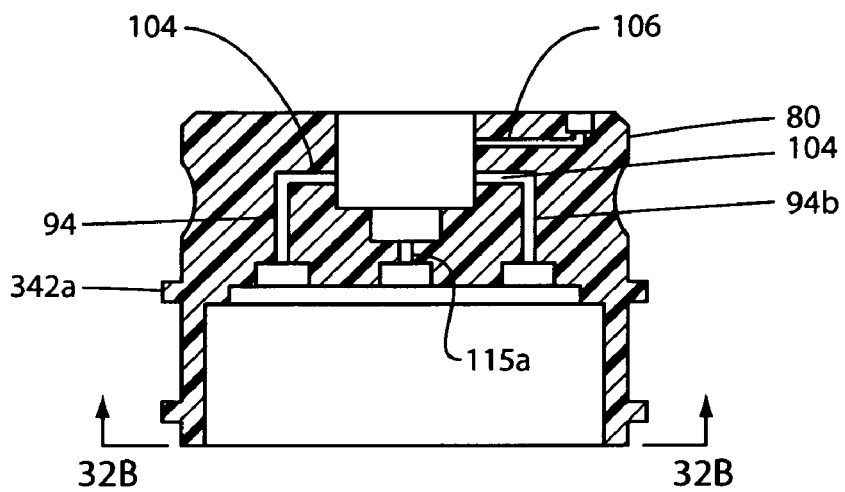
FIG. 33A is an enlarged, cross-sectional view of the selector housing of the device that houses the device selector member for selecting the rate of fluid flow from the fluid reservoir.
Figure 33B:
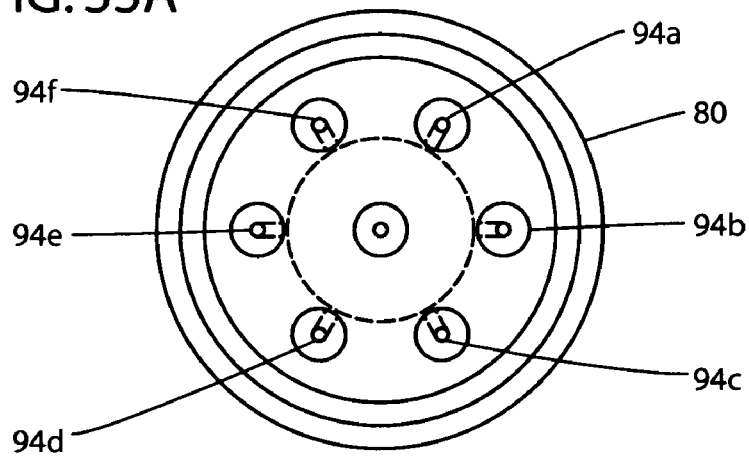
FIG. 33B is a view taken along lines 33B-33B of FIG. 33A.
Figure 33C:
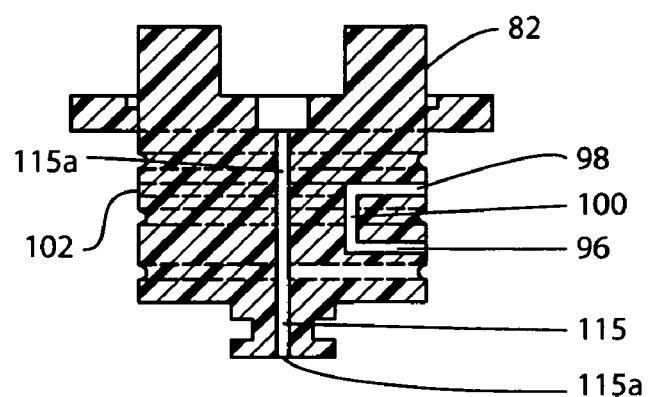
FIG. 33C is a greatly enlarged cross-sectional view of one form of the selector member of the fluid delivery device.

As best seen by referring to FIGS. 33 and 33C, selector member 82 is provided with an inlet passageway 96 and an outlet passageway 98 that is interconnected with inlet passageway 96 by means of an axially extending stub passageway 100 which, in turn, is connected to a circumferentially extending channel passageway 102 formed in selector member 82 (FIG. 33C). With this construction, by rotating the selector member 82, inlet passageway 96 can be selectively brought into index with one of the radial extensions 104 of the axially extending passageways formed in selector member housing 82 thereby providing fluid communication between outlet passageway 98 and the selected one of the circuitous flow passageways formed in rate control plate 86 via annular channel passageway 102 and the selected axially extending passageway formed in the selector member housing 80. Since outlet passageway 98 is in fluid communication with the administration set 58 of the invention via passageway 106 (FIG. 33A), the rate of fluid flow toward the patient can be precisely controlled by selecting a rate control passageway of appropriate configuration and length that is formed in rate control plate 86.

More particularly, the desired flow rate can be selected by controllably rotating the selector member 82, which is secured in position by a selector member retainer component 110, to the desired flow rate indicated by the indicia "I" that is imprinted on the selector member retainer component 110 (see FIG. 33).

To recover any medicament that may remain in reservoir 35 following the fluid delivery step, a pierceable septum 113, which is carried by selector member 82, can be conveniently pierced using a conventional syringe, or like apparatus (not shown). Piercing of septum 113 opens communication between reservoir 35 and the syringe via inlet 115a of a central passageway 115, via the rate control assembly 84, via passageway 115a and via passageway 40b of penetrating member 40a so that any remaining medicament can be readily extracted from reservoir 35.

It is to be noted that the movable components of the dispensing apparatus typically carry conventional "O"-rings to provide appropriate sealing of the components within the apparatus with their mating parts. Throughout the drawings these "O"-rings are identified as "O".

In the present form of the invention, administration set 58, which comprises a part of the dispensing means of the invention for delivering medicinal fluids to the patient, includes, in addition to administration line 58a, a conventional "Y"-site injection septum or port 58b, a conventional gas vent and particulate filter 58c and a line clamp 58d. Provided at the distal end of the administration line is a Luer connector 58e of conventional construction (FIG. 3) which enables the apparatus to be interconnected with the patient in a conventional manner.

Figure 35:
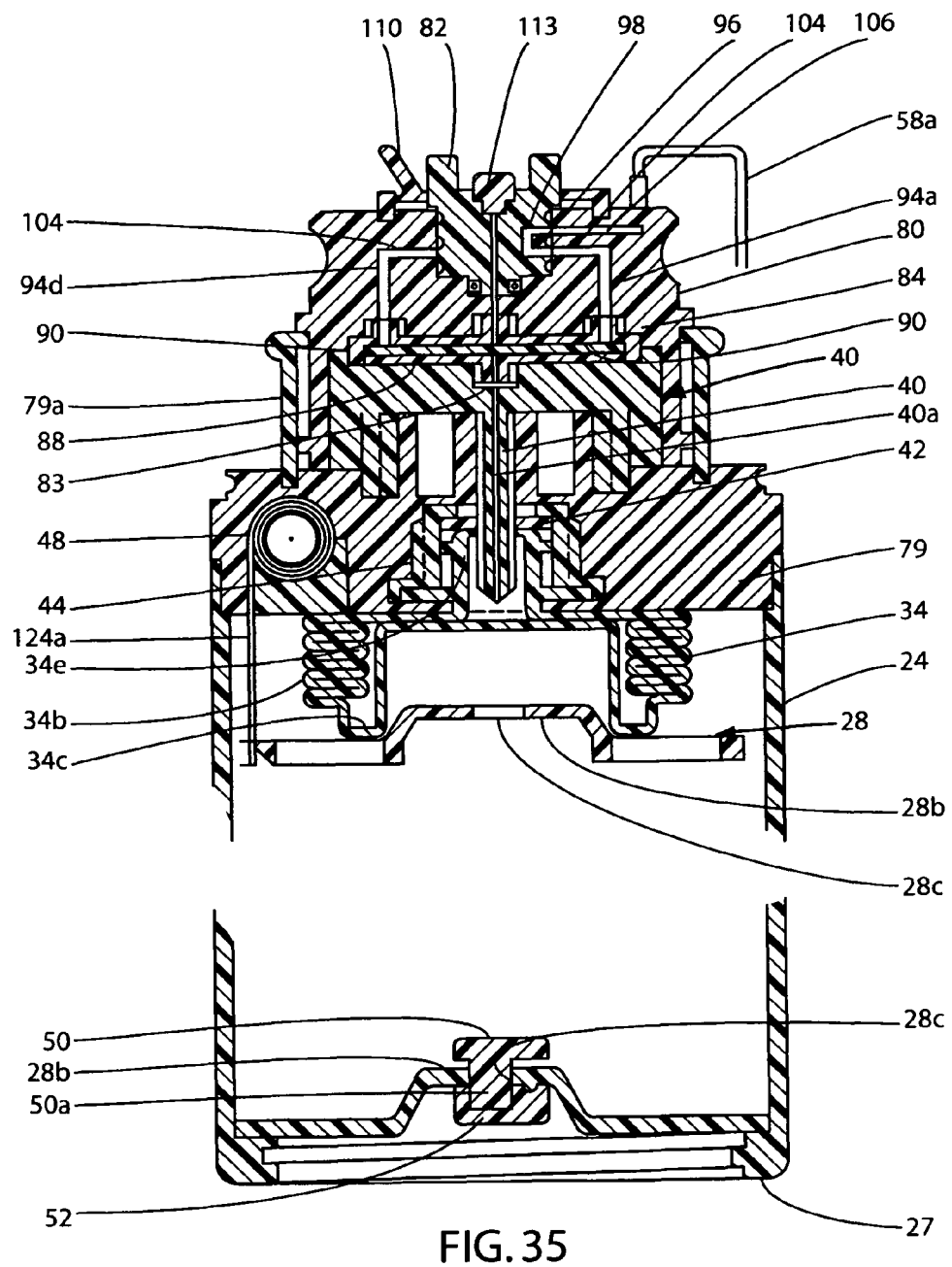
FIG. 35 is a foreshortened, longitudinal, cross-sectional view, similar to FIG. 34, but showing the various components of the alternate form of the apparatus as they appear following delivery to the patient of the fluid contained within the device reservoir with the reservoir substantially empty.

Turning now to FIGS. 34 and 35, an alternate form of the apparatus of the invention is there shown and generally identified by the numeral 120. This form of the apparatus is similar in many respects to the embodiment illustrated in FIGS. 1 through 5 of the drawings and like numerals are used in FIGS. 34 and 35 to identify like components. The primary difference between this alternate embodiment of the invention and the earlier described embodiments resides in the differently configured stored energy means. In this latest form of the invention, the stored energy means comprises a plurality of circumferentially spaced variable force springs 124 that are somewhat similar to prior art constant force springs, but comprise an elongated band, or strip portion 124a that is coiled about a spring drum 126 in predetermined varying degrees of tightness in the manner illustrated in FIGS. 36 and 36A of the drawings. Accordingly, like the earlier described variable force springs in which the elongated band or strip portion of the spring has been modified to exhibit a cross-sectional mass that varies along the length of the band, springs with a variation of coil tightness can produce highly specific and desirable linear and non-linear force-distention curves to meet the fluid delivery requirements of the invention. This type of "inter-wound negative gradient" spring has no slot. In fact, the winding process is done precisely to create a "negative gradient" so that as the spring retracts, it provides a higher force.

As in the earlier described embodiments of the invention, the latest form of the apparatus of the invention comprises a supporting structure 22, which includes a housing 24 having an upper portion 25 and a generally cylindrically shaped skirt portion 26. Disposed within skirt portion 26, is a carriage assembly 28 which is substantially identical in construction and operation to that previously described. As before, the carriage assembly is movable between a first position shown in FIG. 34 and a second position shown in FIG. 35. Carriage assembly 28 here comprises a carriage 30 having a carriage flange 30a to which the novel stored energy means of this latest form of the invention is operably interconnected. Carriage assembly 28 is releasably locked in its first position by a locking means that is also substantially identical in construction and operation to that previously described.

Carried by carriage assembly 28 is a reservoir defining assembly 34 that defines a fluid reservoir 35. Once again, reservoir defining assembly 34 is substantially identical in construction and operation to that previously described. In this latest embodiment of the invention, fluid reservoir 35 is accessible via a penetrating member 40a that is carried by the septum-penetrating assembly generally designated in FIG. 34 by the numeral 40. Penetrating member 40a is adapted to pierce closure wall 39 as well as a pierceable membrane 42 which is positioned over closure wall 39 by means of a closure cap 44 which is affixed to the neck portion 34c of the container assembly (see also FIGS. 7 and 8).

Figure 9:
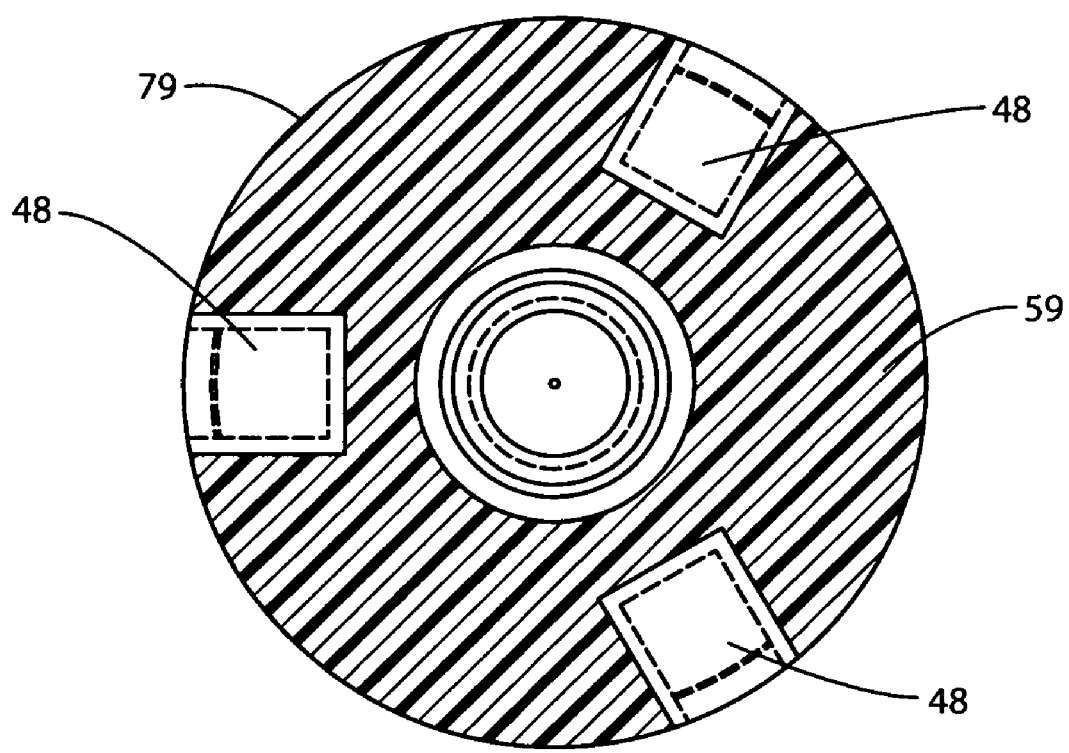
FIG. 9 is a view taken along lines 9-9 of FIG. 4.
Figure 36:
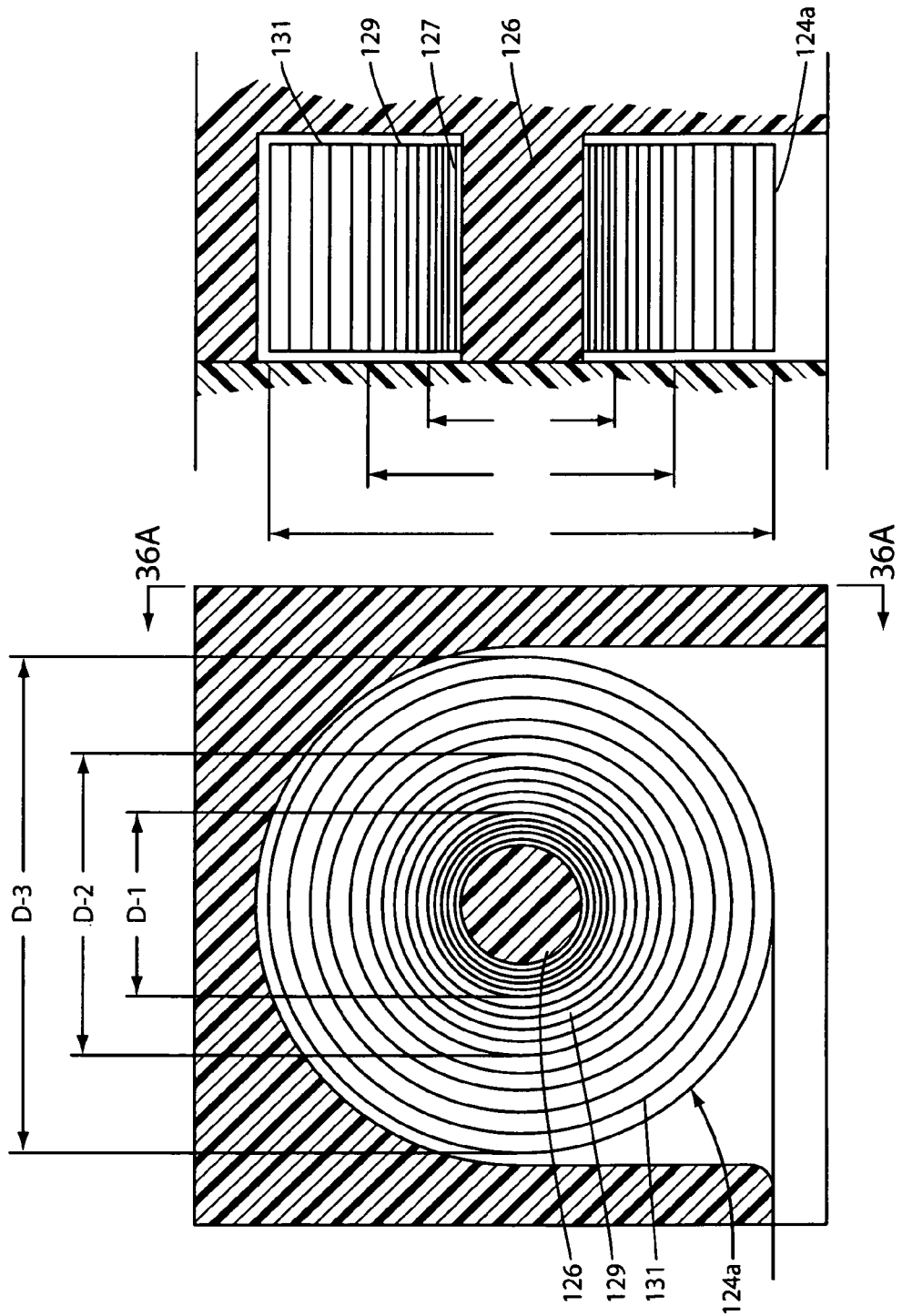
FIG. 36 is a greatly enlarged cross-sectional view of one of the springs and spring drums shown in FIG. 34.

To controllably move the carriage assembly 28 from its first position to its second position, novel stored energy means are provided. This novel stored energy means, which is operably associated with carriage assembly, is here provided in the form of the three previously mentioned, circumferentially spaced, uniquely formed variable force springs 124 that are located within the device housing in the same manner as depicted in FIG. 9. With regard to the variable force springs 124 of this latest form of the invention, the elongated band or strip portion 124a of the spring is coiled about a spring drum 126 in predetermined varying degrees of tightness. More particularly, as depicted in FIGS. 36 and 36A of the drawings where one example of the coiling method is illustrated, the band portion of the spring is initially wound tightly about the drum 126 to produce a first segment 127 having a diameter "D-1". This done, the band portion is then coiled, or wound more loosely about the drum 126 to produce a second segment 129 having a diameter "D-2". Finally, the band portion is coiled, or wound even more loosely about the drum 126 to produce a third segment 131 having a diameter "D-3".

By coiling the springs about their respective drums with a variation of coil tightness in the manner described in the preceding paragraph and as illustrated in FIGS. 36 and 36A, springs having highly specific and desirable linear and non-linear force-distention curves can be produced which will meet the fluid delivery requirements of the invention.

Spring assemblies, such as those depicted in FIGS. 36 and 36A of the drawings that exhibit a variation of coil tightness that produce highly specific and desirable linear and non-linear force-distention curves to meet the fluid delivery requirements of the invention, are available by custom order from various sources, including Vulcan Mfg. & Spring Company of Telford, Pa.

Figure 37:
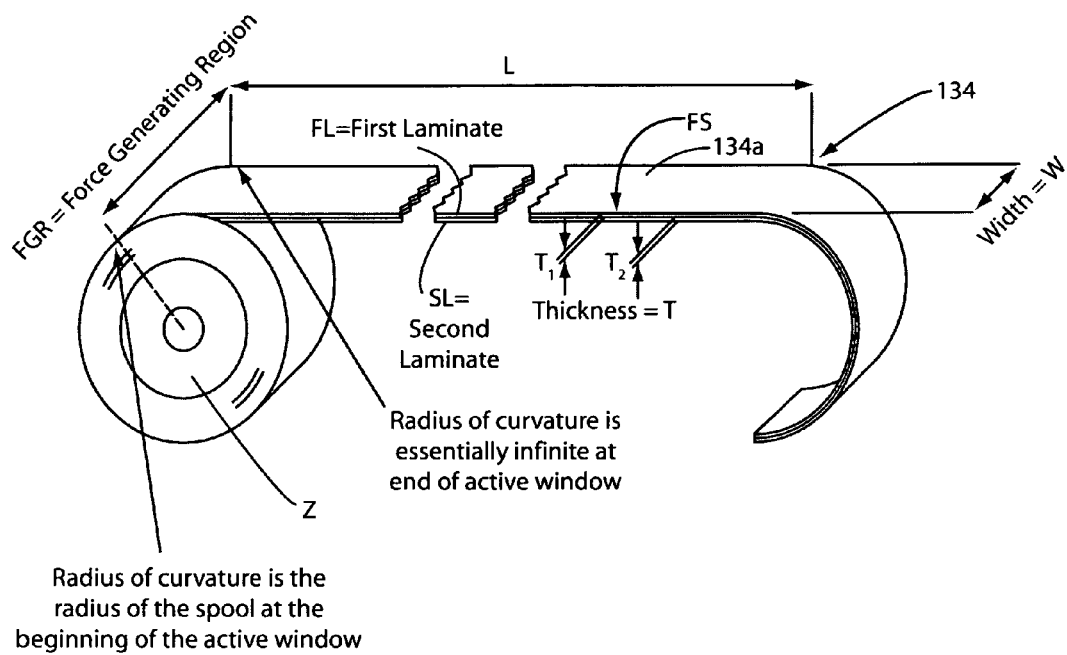
FIG. 37 is a generally perspective view of still another form of modified spring of the invention that is usable with the apparatus shown in FIGS. 34 and 35.

Turning now to FIG. 37 of the drawings, still another form of variable force spring that can be used with the apparatus illustrated in FIGS. 34 and 35. This spring, which is generally identified by the numeral 134, is of a novel laminate construction. This latter form of the retractable spring of a modified configuration is somewhat similar to that shown in FIG. 11 of the drawings, but here comprises a novel laminate construction made up of a first laminate FL and a second interconnected laminate SL. As in the spring of FIGS. 36 and 36A, the elongated band or strip portion 134a of the spring is coiled about a spring drum Z in predetermined varying degrees of tightness. Accordingly, like the earlier described variable force springs in which the elongated band or strip portion of the spring has been modified to exhibit a cross-sectional mass that varies along the length of the band, springs with a variation of coil tightness such as illustrated in FIGS. 36 and 36A, can produce highly specific and desirable linear and non-linear force-distention curves to meet the fluid delivery requirements of the invention. As before, this type of "inter-wound negative gradient" spring has no slot. In fact, the winding process is done precisely to create a "negative gradient" so that as the spring retracts, it provides a higher force. Laminate springs with a variation of coil tightness that produce highly specific and desirable linear and non-linear force-distention curves to meet the fluid delivery requirements of the invention are also available by custom order from various sources, including Vulcan Mfg. & Spring Company of Telford, Pa.

As in the earlier described embodiments of the invention, as the operating member is rotated from a locked position to a release position, the stored energy means, or springs 124 will move the carriage from a position shown in FIG. 34 into the position shown in FIG. 35 and in so doing will urge the fluid contained within reservoir 35 to flow toward penetrating member 40a, into passageway 40b formed in the penetrating member and toward the rate control means of the invention.

The operation of this latest form of the apparatus of the invention is similar to that previously described in connection with the previously illustrated and described embodiments of the invention. With the apparatus in the configuration shown in FIG. 34 and with the fluid reservoir 35 filled with the medicament or diluent to be dispensed to the patient, the dispensing operation can be commenced by first removing the top cover 77. With the cover removed as depicted in FIG. 35 of the drawings, the administration line 58a of the administration set 58 can be unwrapped from the guide sleeve 79a that extends from connector member 79 and about which it has been coiled (see FIG. 34).

To control the flow of medicinal fluid from reservoir 35 toward the administration set 58 of the invention and then on to the patient, the flow control means are operated in the manner previously described.

Once the carriage locking means of the invention, which also comprises a part of the operating means of the invention, has been manipulated in the manner previously described to release the carriage 28, the carriage will move upwardly due to the urging of the variable force springs 124 and in so doing will collapse the container 34 in the manner shown in FIG. 35 of the drawings. As the container collapses, the fluid contained within reservoir 35 will flow outwardly of the reservoir through the outlet 36, into the passageway 40b of the piercing member 40a, through a filter 82 which is carried by the septum-penetrating assembly 40 and then onward toward the rate control assembly 84 of the rate of control means of the invention.

As in the earlier described embodiments of the invention, the desired flow rate can be selected, by controllably rotating the selector member 82 which is secured in position, by a selector member retainer component 110, to the desired flow rate indicated by the indicia "I" that is imprinted on the selector member retainer component 110.

As before, to recover any medicament that may remain in reservoir 35 following the fluid delivery step, a pierceable septum 113 which is carried by selector member 82, can be conveniently pierced using a conventional syringe, or like apparatus (not shown). Piercing of septum 113 opens communication between reservoir 35 and the syringe via inlet 115a of a central passageway 115, via the rate control assembly 84, via passageway 115a and via passageway 40b of penetrating member 40a, so that any remaining medicament can be readily extracted from reservoir 35.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

The invention claimed is:

1. A fluid delivery device for dispensing medicaments to a patient comprising:
   (a) a supporting structure;
   (b) a pre-filled collapsible container containing the medicaments to be dispensed to the patient, said container having a continuous wall formed of a single material carried by said supporting structure, said collapsible container comprising an hermetically sealed reservoir having a continuous wall formed of a single material, said continuous wall comprising a bellows-like side wall, a neck portion connected to said bellows-like side wall and a bottom wall integrally formed with said side wall, said bottom wall including a cup-shaped portion which, upon collapse of said collapsible container, is disposed in close proximity to said neck portion, said hermetically sealed reservoir having an outlet port and including sealing means for sealing said outlet port; and
   (c) stored energy means carried by said supporting structure and operably associated with said collapsible container to deliver a nonlinear force tending to collapse said reservoir to expel fluid therefrom, said stored energy means comprising a spring drum and a spring having an elongated pre-stressed strip, said elongated pre-stressed strip portion being coiled about said spring drum in predetermined varying degrees of tightness and after being wound about said spring drum, said spring will retract in a manner to deliver a nonlinear force tending to collapse said fluid reservoir.

2. The device as defined in claim 1 in which said elongated, pre-stressed strip of spring material is wound about said spring drum in a manner to create a negative gradient so that as said spring retracts, said spring will provide an increasing force tending to collapse said fluid reservoir.

3. The device as defined in claim 1 in which said elongated, pre-stressed strip of spring material is constructed from steel.

4. The device as defined in claim 1 in which said sealing means comprises a pierceable member.

5. The device as defined in claim 1 in which said pre-filled collapsible fluid reservoir is aseptically filled and sealed at time of manufacture.

6. The device as defined in claim 1, further including fluid flow control means carried by said supporting structure for controlling fluid flow from said collapsible reservoir.

7. The device as defined in claim 6 in which flow control means comprises rate control means for controlling the rate of fluid flow from said collapsible reservoir.

8. A fluid delivery device for dispensing medicaments to a patient comprising:
   (a) a supporting structure comprising a base assembly and a housing interconnected with said base assembly;
   (b) a carriage assembly interconnected with said supporting structure for movement between a first position and a second position;
   (c) a unitary, pre-filled, collapsible container having an uninterrupted wall carried by said carriage assembly, said collapsible container comprising a reservoir having an outlet port;
   (d) a stored energy means operably associated with said carriage assembly for moving said carriage assembly between said first and second positions, said stored energy means comprising a spring drum and a spring having an elongated pre-stressed strip of spring material, said elongated pre-stressed strip of spring material of said spring being coiled about said spring drum in predetermined varying degrees of tightness so as to deliver a non-linear force tending to move said carriage assembly between said first and second positions;
   (e) an administration set, including an administration line interconnected with said outlet port of said collapsible reservoir; and
   (f) fluid flow control means carried by said supporting structure for controlling fluid flow from said collapsible reservoir toward said administration set; said fluid flow means comprising operating means including:
       (i) a threaded selector member housing, movable between first and second positions;
       (ii) a tear strip carried by said threaded selector means for retaining said threaded selector member housing in said first position; and
       (iii) a penetrating member operably associated with said threaded selector member for penetrating said top wall of said collapsible container upon movement of said threaded selector member into said second position.

9. The device as defined in claim 8 in which said spring comprises first and second interconnected laminates.

10. The device as defined in claim 8 in which said first end of said elongated, pre-stressed strip of spring material is connected to said carriage.

11. The device as defined in claim 8 in which said flow control means comprises rate control means for controlling the rate of fluid flow from said collapsible reservoir toward said administration set.

12. The device as defined in claim 11 in which said rate control means includes selector means for selecting the rate of fluid flow between said collapsible reservoir and said administration set.

13. The device as defined in claim 12 in which said selector means comprises a selector housing carried by said supporting structure and a selector member rotatably carried by said selector housing.

14. A fluid delivery device for dispensing medicaments to a patient comprising:
   (a) a supporting structure comprising a base assembly and a housing interconnected with said base assembly;
   (b) a carriage assembly interconnected with said supporting structure for movement between a first position and a second position;
   (c) a unitary pre-filled collapsible container having an uninterrupted wall carried by said carriage assembly, said collapsible container comprising a reservoir having an outlet port and a continuous wall comprising a bellows-like side wall, a neck portion connected to said bellows-like side wall and a bottom wall integrally formed with said side wall, said bottom wall including a cup-shaped portion which, upon collapse of said collapsible container, is disposed in close proximity to said neck portion, said hermetically sealed reservoir having sealing means for sealing said outlet port;
   (d) a stored energy means operably associated with said carriage assembly for moving said carriage assembly between said first and second positions, said stored energy means comprising a spring drum and a spring comprising an elongated, pre-stressed strip of spring material having a first end and a second end, said pre-stressed strip of spring material being initially wound tightly about said spring drum to produce a first segment having a first diameter, then being wound about said spring drum to produce a second segment having a second diameter larger than said first diameter and finally being wound about said spring drum to produce a third segment having a diameter greater than said second diameter;

(e) an administration set, including an administration line interconnected with said outlet port of said collapsible reservoir; and (f) fluid flow control means carried by said base assembly of said supporting structure for controlling fluid flow from said collapsible reservoir toward said administration set; said fluid flow means comprising operating means including:

(i) a threaded selector member housing, movable between first and second positions;

(ii) a tear strip carried by said threaded selector means for retaining said threaded selector member housing in said first position; and (iii) a penetrating member operably associated with said threaded selector member for penetrating said top wall of said collapsible container upon movement of said threaded selector member into said second position.

15. The device as defined in claim 14, further including locking means carried by said supporting structure for locking said carriage assembly in said first position.

16. The device as defined in claim 14 in which said uninterrupted wall of said collapsible container is generally accordion-shaped.

17. The device as defined in claim 14 in which said collapsible container comprises a hermetically sealed reservoir.

18. The device as defined in claim 14 in which said first end of said elongated, pre-stressed strip of spring material is connected to said carriage.

19. The device as defined in claim 14 in which said spring comprises first and second interconnected laminates.

20. The device as defined in claim 14 in which said flow control means comprises rate control means carried by said supporting structure for controlling the rate of fluid flow from said collapsible reservoir toward said administration set.

* * * * *